US009499588B2

(12) United States Patent
Mason et al.

(10) Patent No.: US 9,499,588 B2
(45) Date of Patent: Nov. 22, 2016

(54) FLAVIVIRUSES EXPRESSING THE PRM, E, AND NS1 PROTEINS OF OTHER FLAVIVIRUSES AND USES THEREOF

(75) Inventors: Peter W. Mason, Somerville, MA (US); Tomohiro Ishikawa, Kobe (JP)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 13/136,081

(22) Filed: Jul. 22, 2011

(65) Prior Publication Data

US 2011/0311579 A1 Dec. 22, 2011

Related U.S. Application Data

(63) Continuation-in-part of application No. PCT/US2010/000186, filed on Jan. 25, 2010.

(60) Provisional application No. 61/205,803, filed on Jan. 23, 2009.

(51) Int. Cl.
*C12N 7/00* (2006.01)
*C07K 14/005* (2006.01)
*A61K 39/00* (2006.01)

(52) U.S. Cl.
CPC ............... *C07K 14/005* (2013.01); *C12N 7/00* (2013.01); *A61K 2039/5254* (2013.01); *A61K 2039/5256* (2013.01); *A61K 2039/555* (2013.01); *C12N 2770/24122* (2013.01); *C12N 2770/24143* (2013.01); *C12N 2770/24161* (2013.01)

(58) Field of Classification Search
CPC ............. A61K 2039/5254; A61K 2039/5256; A61K 2039/555; C07K 14/005; C12N 7/00; C12N 2770/24122; C12N 2770/24143; C12N 2770/24161
See application file for complete search history.

(56) References Cited

U.S. PATENT DOCUMENTS 6,184,024 B1   2/2001 Lai et al.
6,416,763 B1 *  7/2002 McDonell et al. ........ 424/218.1
2004/0223979 A1 * 11/2004 Chambers et al. ........ 424/199.1

* cited by examiner

*Primary Examiner* — Stacy B Chen
(74) *Attorney, Agent, or Firm* — Norton Rose Fulbright US LLP

(57) ABSTRACT

This invention provides flavivirus vaccines that comprise live-attenuated flaviviruses and methods of making and using these vaccines. The flavivirus vaccines described herein possess higher potency due to in situ production of additional immunogens in a way that mimics viral infection and the vaccines have potential for higher potency, reducing costs for production and delivery.

6 Claims, 9 Drawing Sheets

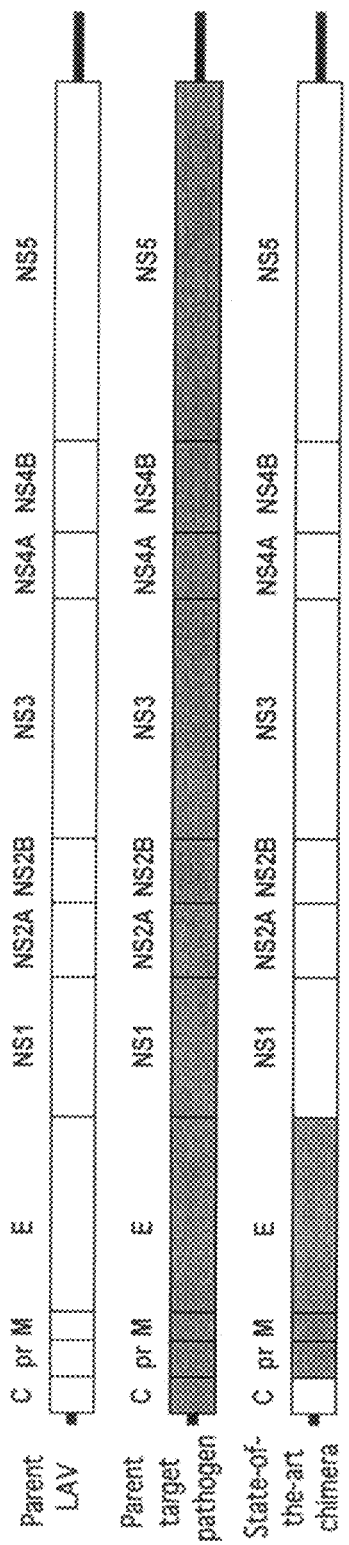
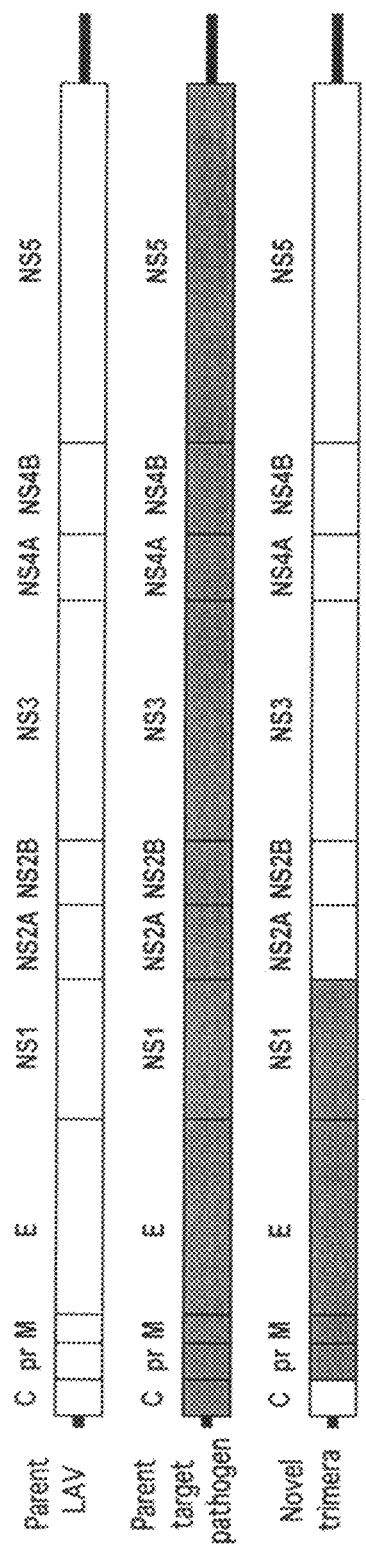
FIG. 1A
FIG. 1B

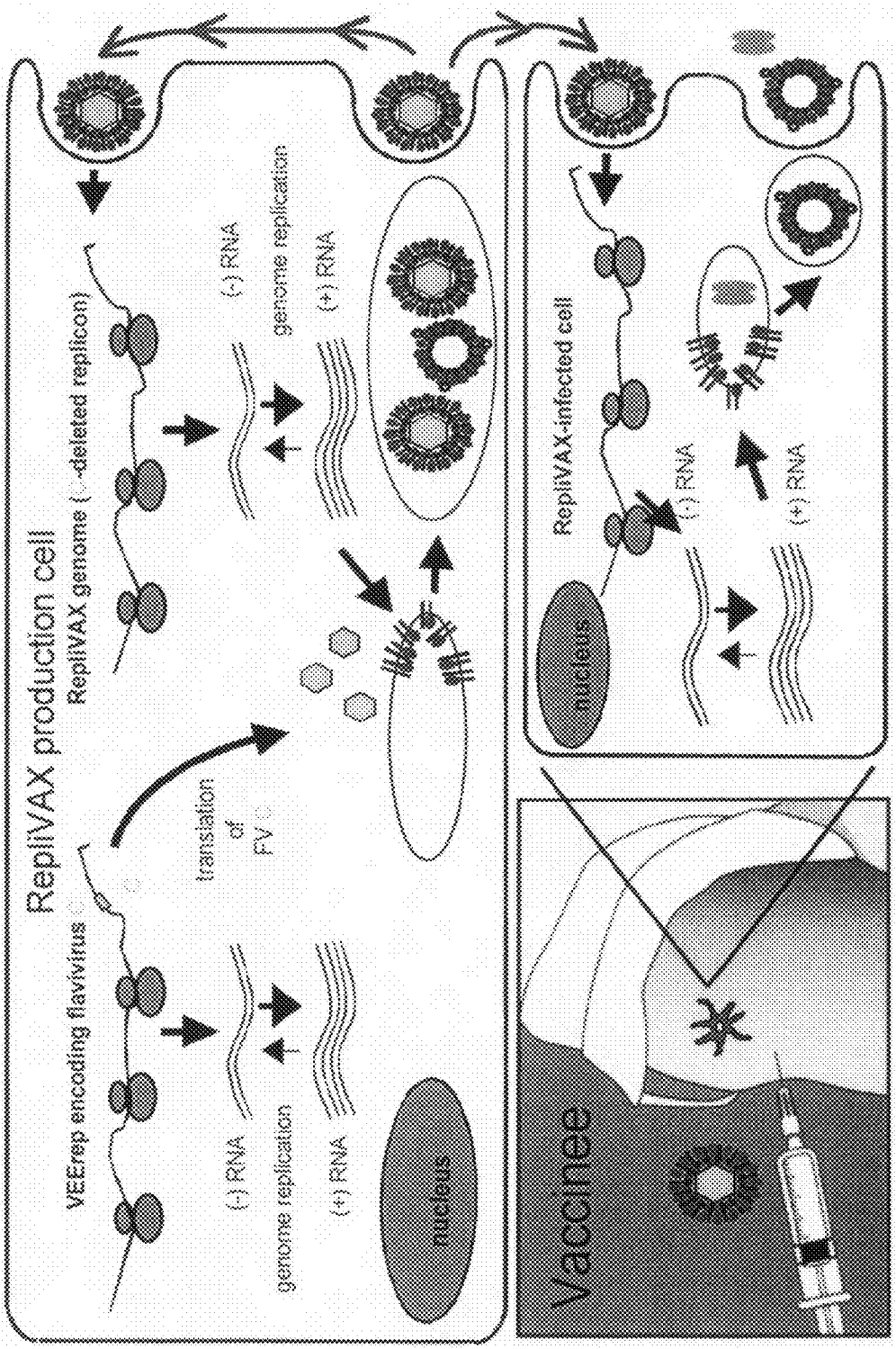

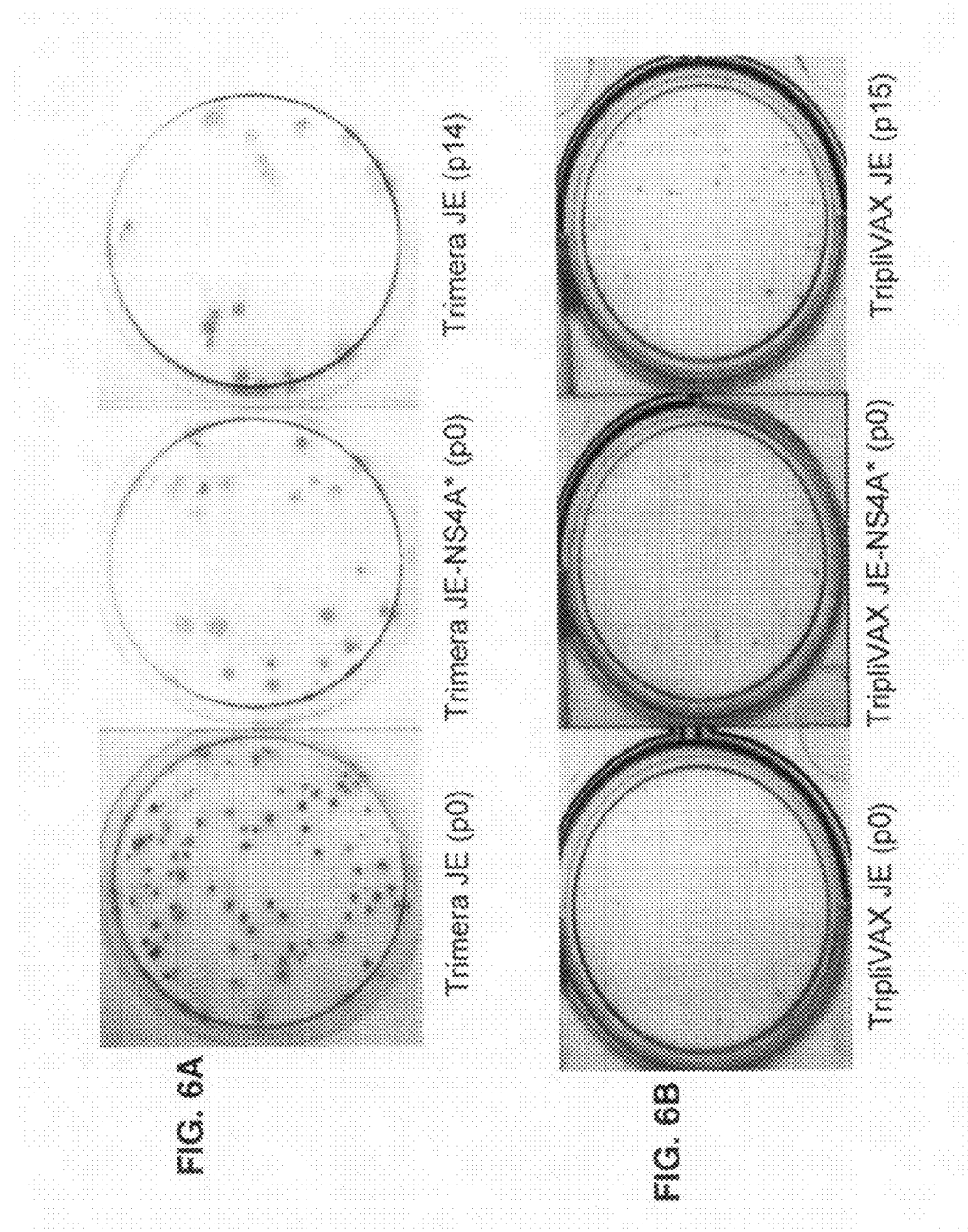

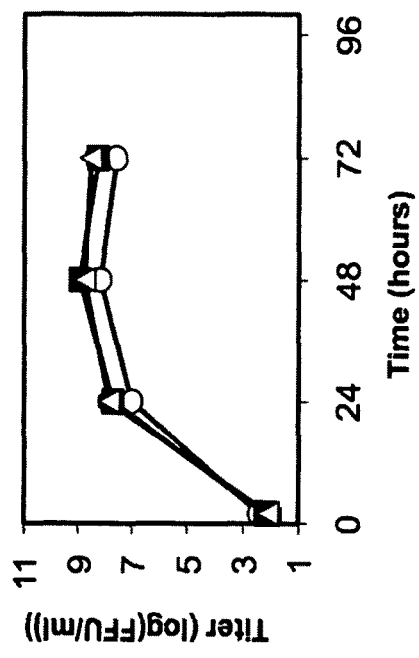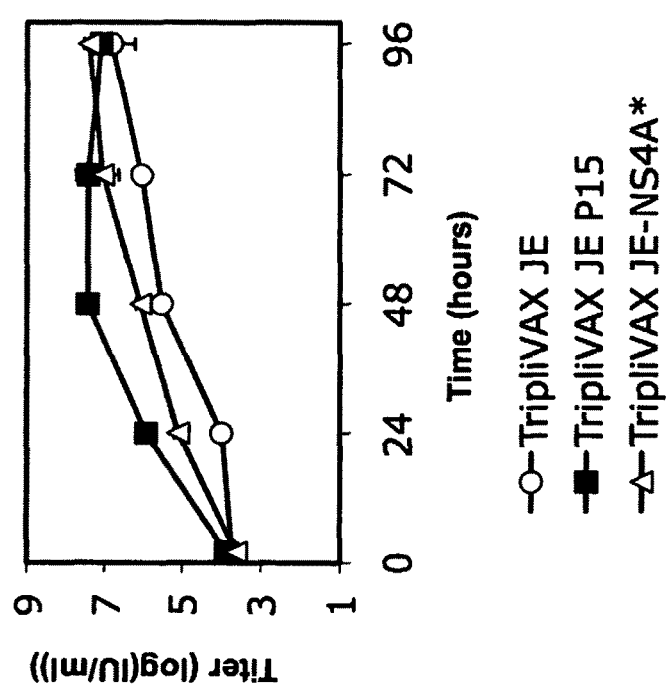

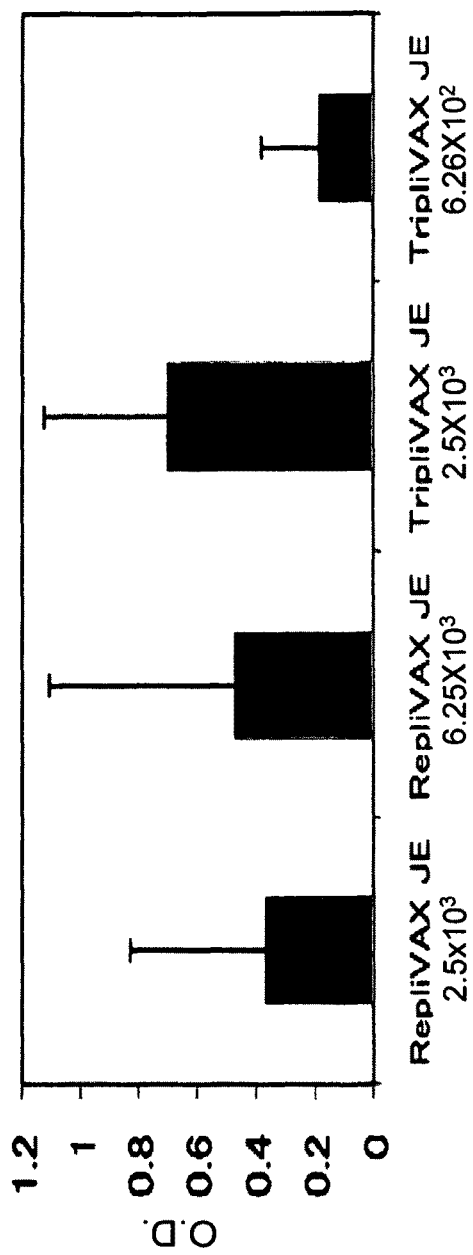
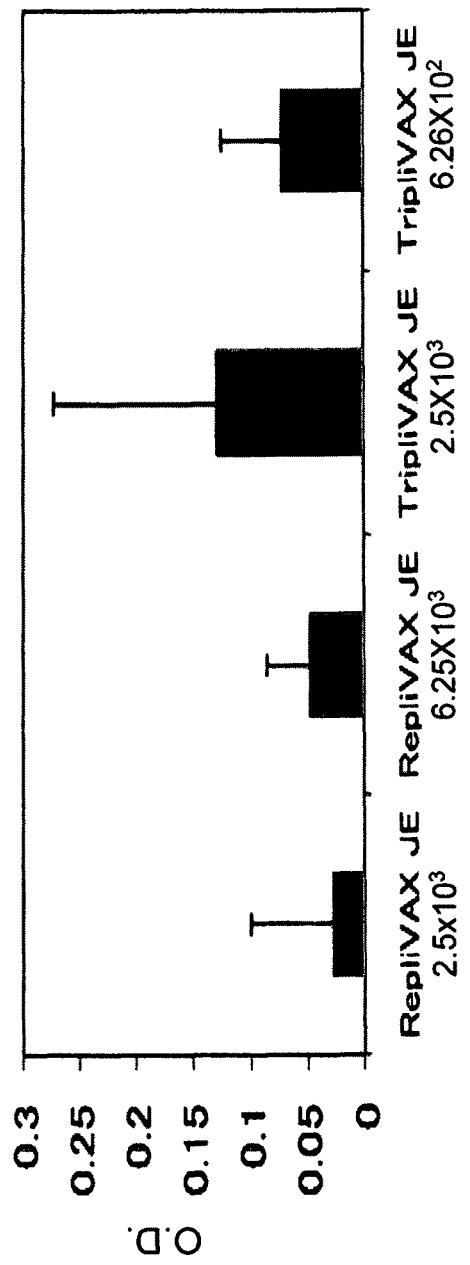
Fig. 9A
Fig. 9B

FLAVIVIRUSES EXPRESSING THE PRM, E, AND NS1 PROTEINS OF OTHER FLAVIVIRUSES AND USES THEREOF

CROSS-REFERENCE TO RELATED APPLICATIONS

This application is a continuation-in-part application claiming benefit of priority under 35 U.S.C. §120 of pending international application PCT/US2010/000186, filed Jan. 25, 2010, which claims benefit of priority under 35 U.S.C. §119(e) of provisional application U.S. Ser. No. 61/205,803, filed Jan. 23, 2009, the entirety of both of which are hereby incorporated by reference.

FEDERAL FUNDING LEGEND

This invention was produced in part using funds obtained through grants U54AI057156 and R21AI77077 from the National Institutes of Health. Consequently, the federal government has certain rights in this invention.

BACKGROUND OF THE INVENTION

1. Field of the Invention

The invention relates to the field of medicine. In particular, it relates to vaccines against flaviviruses and to methods of producing the same.

2. Description of the Related Art

The arthropod-borne flaviviruses are emerging public health problems worldwide. These viruses also pose threats as agents of biowarfare and/or bioterrorism. Japanese encephalitis virus (JEV) is estimated to produce over 50,000 cases of CNS disease a year, about one-third of which result in death (2), making it the flavivirus that causes the highest worldwide mortality.

There is an efficacious inactivated viral vaccine (INV) for Japanese encephalitis virus, but its production has been halted due to adverse events (3). New Japanese encephalitis virus inactivated viral vaccines are in development, and a live-attenuated virus vaccine (LAV) for Japanese encephalitis virus in use in China for decades, has recently been used in other developing countries. There is also a well-characterized rhesus macaque model where JE-INV potency and efficacy correlate with human vaccine potency and efficacy. Large urban epidemics of yellow fever (YF) that plagued tropical and subtropical regions until the early 1900s have been eliminated by mosquito control and application of the efficacious YF-17D live-attenuated virus vaccine.

Although originally thought to be very safe, an alarming number of cases of yellow fever (referred to as acute viscerotropic disease from yellow fever vaccination—YEL-AVD) have been associated with recent yellow fever-17D vaccination campaigns, suggesting that a safer vaccine is needed. Of particular concern are analyses of the viruses recovered from some cases of YEL-AVD (which displayed severe symptoms of hemorrhagic fever indistinguishable from jungle YF) that failed to produce evidence that YEL-AVD has been caused by simple reversion of the vaccine virus (4). Thus, YF-17D vaccine quality control systems similar to those implemented by the WHO in responses to YF-17D-associated neurological disease caused by revertant viruses several decades ago (5,6) are unlikely to be able to make the current YF-17D vaccine safer.

Dengue includes a spectrum of illnesses caused by infection with one of four serotypes of Dengue virus (types 1-4) that occur in many tropical and subtropical regions. The geographic distribution of dengue has expanded over the last 30 years to include more than 100 countries (7). Based on the number of infections with Dengue virus (estimated to be 50 million per year) and the fact that there are 100s-of-thousands of cases of severe dengue each year (7), Dengue virus is considered the most important arthropod-borne virus (7). In some cases, Dengue virus produces a sub-clinical infection, but a febrile illness, dengue fever (DF) occurs in many infected individuals. A portion of dengue fever patients, develop more severe syndromes such as dengue hemorrhagic fever (DHF).

Live-attenuated virus vaccine and inactivated viral vaccine for dengue are in development, but to date, no dengue vaccines have progressed beyond clinical trials, and unique aspects of immunopathogenesis of dengue (8) are problematic for most vaccines in development. No vaccines exist for diseases caused by West Nile virus (WNV), which is responsible for the largest epidemic of viral encephalitis in United States history.

The flavivirus genome is a positive-sense, single-stranded, non-poly(A) RNA of ~11 kb in length that can initiate infection in the absence of viral proteins. The genome is translated as a single polyprotein that is co- and post-translationally processed by the combined actions of viral and cellular proteases. The 5' quarter of the genome encodes the structural proteins: capsid (C), membrane (M) (produced from its precursor, prM), and envelope (E). The remaining three quarters of the genome encodes non-structural proteins that replicate the genome, process viral proteins, promote virus assembly, and interact with the host cell. The flavivirus virion is a 50 nm particle consisting of a nucleocapsid surrounded by a lipid bilayer containing E and M. The nucleocapsid, which consists of C and the RNA genome, buds through prM/E-studded patches of the endoplasmic reticulum membrane to produce provirions, which accumulate within the cell's secretory pathway. As these particles transit the secretory pathway of the cell, they mature into viral particles as prM is cleaved to M by a cellular protease (furin). Expression of prM/E in eukaryotic cells results in secretion of 20-30 nm sub-viral particles (SVPs) that share properties with a natural by-product of flavivirus infection (9). Sub-viral particles consist of lipid bilayers containing M and E without C or any genetic material. Sub-viral particles have been demonstrated to be useful subunit vaccines (10), and these particles are considered to be key components produced by many efficacious vaccine candidates (9,11-14).

Flavivirus vaccines in development share problems with existing vaccines. Current inactivated viral vaccine {including the Japanese encephalitis virus inactivated viral vaccine (2.1) and a tick-borne encephalitis (TBE) inactivated viral vaccine in use in Western Europe}, as well as a replacement Japanese encephalitis virus inactivated viral vaccine (15), require extensive purification, and are of low potency, requiring multiple vaccinations. A new flavivirus subunit vaccine candidate (16,17) may suffer from similar problems. Viral-vectored vaccines, including a recently described alphavirus replicon-vectored vaccine (18) may also suffer from problems of "vector immunity" (19) that interfered with the use of vaccinia virus as a vector for a recombinant DNA-derived Japanese encephalitis virus vaccine candidate (20). DNA vaccines have low potency (21). There may also be problems with existing and new live-attenuated virus vaccines including the chimeras generated from YF-17D that relate to an incomplete understanding of the basis of their attenuation, and a resultant concern that they might prove to be unsafe in a portion of the vaccinated population.

Specifically, for all live-attenuated virus vaccines in development, there are concerns that like YF-17D (2.1), these vaccines may not be safe in all vaccines, especially the immunocompromised, and in this population (or perhaps even in a small subset of normal vaccines) serious disease will result from these "live" virus vaccines.

Humoral immunity plays a critical role in control of flavivirus infections. Mechanisms of antibody-mediated immunity include: blocking viral binding to cells, Fc receptor-dependent viral clearance, and antibody-mediated cytotoxicity. Although immunity to E, which covers the entire surface of the virion (22), appears to be the primary target of neutralizing (NEUT) antibodies (23), multiple studies have demonstrated that antibodies to NS1 can protect from flavivirus disease (24-26). Consistent with the role of humoral immunity in protection, B cell-deficient mice are more susceptible to flavivirus disease than intact animals (27-30) and protection against flavivirus infection in B cell-deficient mice can be partially restored by adoptive transfer of immune splenocytes (28).

Cellular immunity also plays a role in controlling flavivirus infections. Passive transfer of JEV-immune CTLs has been shown to mediate protection from Japanese encephalitis virus in mice (31), and more recent work with WNV has shown that mice with defects in CTL responses have a reduced ability to clear WNV infections (32,33). In addition, mice that have received WNV-specific CD8+ (34,35) or CD4+ T cells (36) are protected from lethal challenge. Also, CTL responses have been detected in human volunteers given candidate vaccines expressing prM/E/NS1 proteins (37). Although, CTL responses may not be as important as humoral immunity in providing protection from disease, they may be particularly helpful in vulnerable populations, such as the elderly, very young and immunocompromised, where antibody may not be sufficient to confer protection from infectious diseases (38).

The innate immune system is the first line of defense against invading pathogens. One key aspect of this system is recognition of pathogen-associated molecular patterns through pattern-recognition receptors that trigger signaling cascades resulting in secretion of cytokines and chemokines that activate antimicrobial mechanisms and direct adaptive immune responses. Current state-of-the-art vaccinology is trying to systematically characterize and harness this innate/adaptive interface, and it seems likely that advances in this area will translate into better vaccines. The current paradigm reiterates "old-school" thinking that there is likely to be a considerable advantage to the use of self-replicating virus-derived vectors for expression of vaccine antigens (e.g., prM/E and NS1 proteins), since the vector "infections" should induce responses that lead to the type of innate immune stimulation that has evolved to produce an effective adaptive immune response. Therefore, such vectors (e.g., RepliVAX) are likely to provide better protection than inactivated viral vaccines or subunit vaccines by mimicking viral infection and thus stimulating more effective immune responses.

The inventors have recognized a need in the art for a new class of flavivirus vaccines that is superior to other flavivirus vaccine technologies. Specifically, the prior art is deficient in flavivirus vaccine that 1) does not cause disease, even in the immunocompromised, 2) has high potency due to in situ production of immunogens in a way that mimics viral infection, 3) has potential for inexpensive production. The present invention fulfills this long-standing need and desire in the art.

SUMMARY OF THE INVENTION

The present invention adds significantly to the utility of "chimeric" live-attenuated virus vaccines for flavivirus diseases. These utility improvements include, but are not limited to, 1) enhanced potency with respect to immune response to E and NS1, 2) reduced interference from existing immunity due to previous flavivirus infection or vaccination, and 3) reduced interference from concurrent vaccination with other live-attenuated virus vaccines from flavivirus diseases. The present invention is directed to a new class of flavivirus vaccines based on genetically engineered live-attenuated virus vaccines, including live-attenuated virus vaccines based on RepliVAX technology. The invention provides a live-attenuated single cycle trimeric flavivirus, that comprises a first flavivirus encoding glycoproteins from a second flavivirus, comprising membrane precursor gene (prM), envelope gene (E) and NS1 protein gene (NS1) from a second flavivirus. The first flavivirus may be any flavivirus that can be used as an live-attenuated virus vaccine. Representative examples of the second flavivirus include but are not limited to Yellow fever virus such as YF-17D yellow fever virus, Dengue virus such as Dengue-1, Dengue-2, Dengue-3 and Dengue-4, West Nile virus or Japanese Encephalitis Virus (JEV).

The invention also provides vaccine compositions that include any of the viruses described herein and a pharmaceutically acceptable carrier or diluent, as well as methods of inducing an immune response to a flavivirus in a patient by administration of such a vaccine composition to the patient. The invention also provides immunogenic compositions comprising the live-attenuated single cycle flavivirus described herein and a packaging cell line expressing a capsid gene. The invention also provides a method of increasing the potency and efficacy of a chimeric live attenuated virus vaccine by addition of NS1 to the chimeric live attenuated virus vaccine, thereby eliciting better immune responses to E and to the relevant NS1. Patients treated using these methods may not have, but may be at risk of developing the flavivirus infection, or may have the flavivirus infection.

BRIEF DESCRIPTION OF THE DRAWINGS

FIG. 1A-AB: schematic diagrams of the genetic structure of flaviviruses. FIG. 1A shows a schematic diagram showing flavivirus chimeras. FIG. 1B shows a schematic diagram showing genetic structure of flavivirus trimera.

FIG. 2A-2B: RepliVAX production and use. FIG. 2A: Production of RepliVAX in a packaging cell encoding the WNV C protein from a non-cytopathic VEE replicon. FIG. 2B: Vaccinated host with a blow-up of a RepliVAX-infected cell producing SVPs and NS1.

FIG. 4A: Average E protein ELISA OD values obtained using previously described methods with 1/100 dilutions of sera. FIG. 4B: Average NS1 protein ELISA OD values obtained using previously described methods with 1/100 dilutions of sera. Extended bars show standard deviations within groups.

FIGS. 6A-6B: Focus comparison of blind passed Trimera JE and TripliVAX JE. FIG. 6A shows focus size of Trimera JE p0 and blind-passed Trimera JE p14 were compared on Vero cells. FIG. 6B shows focus size of TripliVAX JE p0 and blind passed TripliVAX JE p15 were compared on BHK (VEErep/Pac-Ubi-C*) cells. To examine the effects of NS4A mutation on the focus size, Trimera JE-NS4A* and TripliVAX JE-NS4A* were examined using Vero and BHK (VEErep/Pac-Ubi-C*) cells, respectively. All three preparations were compared side by side.

FIGS. 7A-7B: Effects of NS4A mutation on the growth kinetics. In FIG. 7A, growth kinetics of parental Trimera JE (open circle), blind-passed Trimera JE p14 (closed square) and Trimera JE-NS4A* (open triangle) were compared using BHK cells. In FIG. 7B, growth kinetics of parental TripliVAX JE (open circle), blind-passed TripliVAX JE p15 (closed square) and TripliVAX JE-NS4A* (open triangle) were compared using BHK(VEErep/Pac-Ubi-C*) cells.

FIG. 9. Low-dose comparison of TripliVAX JE and RepliVAX JE. Panel shows mouse Serum IgG antibody responses against JEV E (9A) and JEV NS1 (9B) 21 days post-immunization. Bars represent the group mean O.D. and extended bars show SD. The average O.D. obtained from media control (L15)-immunized group was subtracted from those of other groups.

FIG. 10. Effects of pre-existing NS1 immunity on the subsequent TripliVAX JE immunization. Panel shows Mouse serum IgG antibody levels to JEV E (10A) proteins and neutralizing antibody (10B) titers 21 days post-boost immunization. Mice were immunized with media control L15 or WN-NS1-VRPs and then boosted with TripliVAX JE or RepliVAX JE at 21 days post-priming immunization. The dots represent O.D. value or neutralizing antibody titer obtained from individual serum. Triangles represent the average and the extended bars show SD.

DETAILED DESCRIPTION OF THE INVENTION

Figure 3:
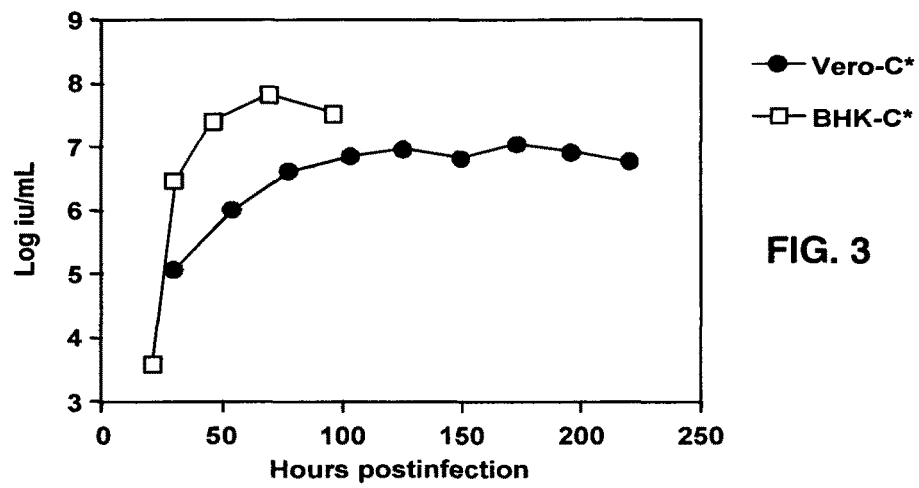
FIG. 3: production of RepliVAX WN by cells expressing VEErep/Pac-Ubi-C*. BHK-C* (in 1% FBS) or Vero-C* (in serum-free media) were infected at an moi of 0.1 and media was replaced at 24 hour intervals and titrated.
Figure 4A:
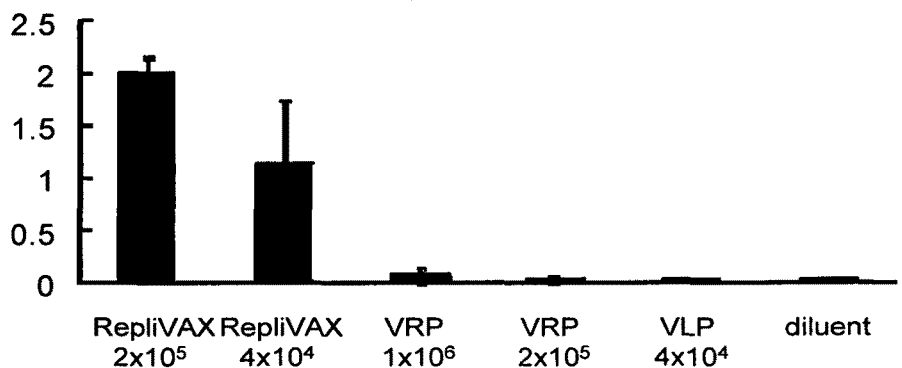
FIG. 4A-4B: ELISA reactivity of sera collected at 21 days post vaccination from hamsters vaccinated with the indicated doses of WNV-derived RepliVAX or VRPs by the ip route.
Figure 4B:
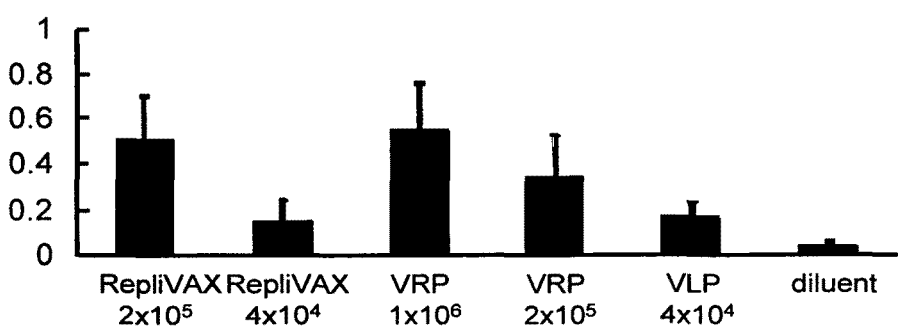
Figure 5:
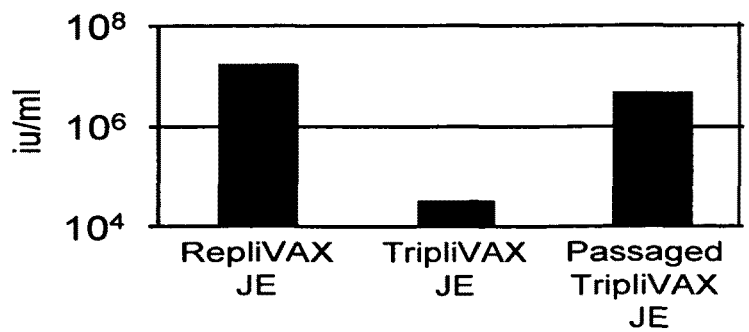
FIG. 5: Adaptive mutations in NS4A were required to enhance the growth of TripliVAX JE. Panel shows a comparison of endpoint titers on C-expressing RepliVAX packaging cells derived from vaccine-compatible Vero cells.

As used herein the specification, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Furthermore, unless otherwise required by context, singular terms shall include pluralities and plural terms shall include the singular.

As used herein, the term "or" in the claims is used to mean "and/or" unless explicitly indicated to refer to alternatives only or the alternatives are mutually exclusive, although the disclosure supports a definition that refers to only alternatives and "and/or."

As described herein, the term "single-cycle flavivirus" refers to a flavivirus that is unable to produce infectious particles in vaccinated animals due to deletion of its capsid (C) gene. As described herein, the terms "chimera" and "chrimeric flavivirus" refer to a type of flavivirus comprising a live-attenuated virus vaccine derived from one flavivirus that expresses flavivirus glycoproteins from a second flavivirus. As described herein, the terms "trimera" and "trimeric flavivirus" refer to a type of chimeric flavivirus vaccine that expresses all three flavivirus glycoproteins from a target pathogen in an LAV derived from another flavivirus.

Flaviviruses cause vaccine-preventable diseases that are responsible for considerable morbidity and mortality worldwide. There are only two types of vaccines for flavivirus disease that are currently approved for use in man. These include live attenuated viral vaccines (LAV), such as the yellow fever virus (YFV) strain 17D (YF 17D strain; used worldwide), and inactivated viral vaccines (INV), such as a formalin-inactivated preparation of Japanese encephalitis virus (JEV) obtained from the brains of virus-infected mice. Existing vaccines for flavivirus diseases need improvement, and no vaccines exist for dengue (the flavivirus disease with the highest incidence worldwide) or diseases caused by West Nile virus (WNV; which is responsible for the largest epidemic of viral encephalitis in United States history). Live-attenuated virus vaccines are considered preferable to inactivated viral vaccines due to their economy of production and greater potency than inactivated viral vaccines. Both cost and public health impact are greatly affected by potency, since many inactivated viral vaccines require boosts that are either minimal or unnecessary in the case of live-attenuated virus vaccines.

Live attenuated virus vaccines currently in use have been produced by empirical attenuation (by passage in unnatural systems), but these same methods have failed to produce useful live-attenuated virus vaccines for all four serotypes of dengue and other flaviviruses. Alternatives to these empirically attenuated live-attenuated virus vaccines include genetically derived chimeras based on genetic engineering of other live-attenuated virus vaccines to serve as "vectors" to deliver the envelope proteins of a second flavivirus, producing an live-attenuated virus vaccine that can protect against infections by the second flavivirus. In the case of YF 17D, this technology, referred to as the ChimeriVax technology, was first applied to Japanese encephalitis virus. Briefly, the Japanese encephalitis virus prM and E genes were substituted into the YF 17D genome, producing a new live-attenuated virus vaccine (ChimeriVax JE) that could protect against Japanese encephalitis virus. Construction of these chimeric vaccines was based in part on early studies suggesting that the junctions between E and NS1 were the most fruitful places to construct viable intra-viral chimeras with high replicative ability suitable for LAV strain formulation, and the belief that much of the protective immunity engendered by flavivirus vaccines is due to the immunity afforded by the E protein, especially when expressed as a viral particle or a sub-viral particle (SVP).

However, it has been known for decades that the flavivirus NS1 protein is also an important immunogen and NS1 immunity can prevent flavivirus-induced disease. And, moreover, as such, a genetically engineered chimera of the type shown in FIG. 1 could be rendered less effective in a host carrying immunity to the NS1 protein produced by previous exposure to the "vector" used to create such a chimeric live-attenuated virus vaccine. By extension, multivalent live-attenuated virus vaccines, which seek to induce immunity to multiple flaviviruses (as is envisioned for the required tetravalent vaccine for dengue) would likely be further compromised by NS1 "vector" immunity (if all were derived from a single vector), resulting in competition among the chimeras, producing unequal immunity to all vaccine components.

The instant invention 1) demonstrates that NS1 immunity induced by a special type of single-cycle live-attenuated virus vaccine derived from West Nile Virus is able to provide protection from infection, proving the importance of NS1 immunity to genetically engineered flavivirus vaccines; 2) describes how to generate a new type of chimeric flavivirus vaccine (referred to herein as a "trimera") that expresses all three flavivirus glycoproteins from a target pathogen (in this example Japanese encephalitis virus) in an live-attenuated virus vaccine derived from another flavivirus (in this example West Nile Virus); and 3) demonstrates that trimeras produced by this method provide superior immunity to the target pathogen (in this example Japanese encephalitis virus) than typical chimeras (Table 4).

In some embodiments of the present invention there is provided a live-attenuated trimeric flavivirus, comprising a first flavivirus encoding glycoproteins from a second flavivirus, comprising membrane precursor gene (prM), envelope gene (E) and a NS1 protein gene (NS1) from a second flavivirus, wherein the second flavivirus is different from said first flavivirus. Further to this embodiments, a representative second flavivirus is: 1) a Dengue virus, including but not limited to Dengue-1, Dengue-2, Dengue-3, or Dengue-4 virus; or 2) a Yellow Fever virus, including but not limited to a YF-17D yellow fever virus; or 3) a West Nile virus; or 4) a Japanese Encephalitis Virus. Further to this embodiments, a representative first flavivirus is West Nile Virus, Japanese Encephalitis virus, Yellow Fever virus or Dengue virus.

In another embodiments of the present invention, the live-attenuated trimeric flavivirus contains one or more than one mutation(s) in: 1) amino acid 18 of the NS4A protein; 2) amino acid 29 of the NS4A protein; 3) amino acid 135 of the NS4A protein; 4) amino acid 47 of the prM protein; 5) amino acid 62 of the capsid protein; or a combination thereof. Further to these embodiments, the live-attenuated trimeric flavivirus contains one or more than one mutation(s) consisting of: 1) a glycine to arginine mutation at amino acid 18 of the NS4A protein; 2) a valine to isoleucine mutation at amino acid 29 of the NS4A protein; 3) a valine to methionine mutation at amino acid 135 of the NS4A protein; 4) a aspartic acid to asparagine mutation at amino acid 47 of the prM protein; 5) a threonine to serine mutation at amino acid 62 of the capsid protein; or a combination thereof.

In yet another embodiment of the present invention there is provided a method of inducing an immune response to a pathogenic flavivirus infection in a patient. Further to these embodiments, the method comprises administering to the patient a live-attenuated trimeric flavivirus discussed supra. Further to these embodiments, the patient discussed supra does not have, but is at risk of developing, said flavivirus infection. Further to these embodiments, the patient discussed supra has flavivirus infection.

In yet another embodiment of the present invention there is provided an immunogenic composition comprising the live-attenuated trimeric flavivirus discussed supra and a pharmaceutically acceptable carrier or diluent.

In yet another embodiment of the present invention there is provided a method of increasing the potency and efficacy of a chimeric live attenuated virus vaccine by addition of a NS1 protein gene to the chimeric live attenuated virus vaccine, thereby eliciting better immune responses to E and to the relevant NS1.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Production of Stable Packaging Cells to Safely Propagate RepliVAX

Large-scale production of RepliVAX for human use requires a cell line that: 1) produces high levels of C, supporting high-titer growth of RepliVAX, 2) encodes a C gene that cannot productively recombine with the RepliVAX genome to produce a "live" virus, and 3) can be propagated serially without losing the C gene.

High-level C expression was assured by using a non-cytopathic VEErep (53). Eliminating the ability of RepliVAX WN to recombine with cell-expressed C to produce a genome capable of spreading in the vaccinated host was addressed by three independent methods that produced a modified C gene (C*) unable to recombine with RepliVAX WN. These methods were 1) The C* gene corresponded to the smallest functional fragment of the West Nile Virus genome (the mature C gene), 2) The C* gene contained synonymous mutations in the region overlapping the remnant of C (trC) present in RepliVAX WN; and 3) The synonymous mutations in C* ablated the cyclization sequence (CS) (1).

Stable, long-term expression of C by packaging cells was addressed by fusing C* to a puromycin (Pur) acetyl-transferase gene (Pac) driven by the subgenomic promoter of the VEErep (55), producing replicon VEErep/Pac-Ubi-C*. This fusion reduces the chance of "loss" of the C gene by intermolecular recombination during propagation of VEErep-expressing cells, which has been observed (52).

Pur-resistant BHK cells transfected with VEErep/Pac-Ubi-C* (BHK-C*) were able to produce RepliVAX WN at titers of >$10^7$ infectious units (iu)/ml (FIG. 3). Importantly, when monolayers of passage 8 (p8) and p70 BHK-C* were infected with stocks of RepliVAX WN, no differences were detected in either infectious focus number or size, demonstrating extraordinary phenotypic stability (essential for utility as a master cell stock for human vaccine production). Further, sequencing across the C gene of BHK-C* at p24 failed to detect any changes relative to VEErep/Pac-Ubi-C*, confirming stability (1).

To demonstrate that RepliVAX WN did not recombine with the C gene in BHK-C*, RepliVAX WN was serially passaged (sp) in BHK-C* cells. After sp30, undiluted RepliVAX WN was then blind passaged on Vero cells (to remove contaminating RepliVAX), and the entire second-pass monolayer was stained for viral antigen, revealing no infected cells, thus rigorously demonstrating absence of productive recombination (1).

Since BHK cells are not a suitable substrate for human vaccine manufacture, Vero-C* cells were produced by applying the methods outlined above to human vaccine production-compatible Vero cells (from S. Whitehead, NIH) maintained in serum-free media. These cells, which have maintained their complementing phenotype for dozens of passages, support high levels of production of RepliVAX WN. Although RepliVAX titers obtained on Vero-C* are lower than those achieved with BHK-C*, the Vero-C* did not show cytopathic effect, permitting repeated harvesting {(1) & FIG. 3}. These properties indicate that multiple harvests could be used for vaccine preparation, and suggest that RepliVAX harvests will be low in Vero DNA content, facilitating manufacture and licensure. Although the inexpensive antibiotic Pur is used during routine C* cell passage, the VEErep is maintained in these cells for up to a week in its absence, and Pur is always excluded from cultures during RepliVAX growth.

Taken together, these data demonstrate the high stability of gene expression in these packaging cell lines, lack of infectious virus formation, and high efficiency of RepliVAX packaging into infectious particles in a cell line suitable for preparation of an LAV that could be used in man.

Improvement to the Genetic Structure of RepliVAX WN

RepliVAX WN serially passaged 10 times (sp10) in BHK-C* cells produced polymorphic foci of infection on BHK-C* cells, with many foci 3- to 5-times larger than those produced by unpassaged RepliVAX WN (1). Furthermore, sp10 RepliVAX WN replicated faster than our original RepliVAX WN, with an endpoint titer twice as high (1). Analyses of the trC through prM region of sp10 RepliVAX WN revealed two mutations. As expected from the heterogeneous nature of the sp10 foci, both mutations were present as mixtures. One mutation consisted of an AAG_AtG (K_M) at position P3 following the NS2B/NS3 cleavage site (QKKR|GGK(m)T) in trC. The second mutation consisted of an AGC_tGC (S_C) at a position preceding the prM signal peptidase cleavage site (S(c)VGA|VTLS). Re-derivation of 2nd-generation RepliVAX WN with either mutation demonstrated that either change produced better-growing RepliVAX WN. The re-derived clone containing the S>C mutation in the signal peptidase cleavage site was designated RepliVAX WN.2, and used for all further studies.

Altering NS2B/NS3 and signal peptidase cleavage between C and prM has been shown to influence flavivirus particle yield and infectivity (56-59). Mouse and hamster studies demonstrated 100% protection by a single immunization of RepliVAX WN.2 which produced 90% NEUT antibody titers of 1:40 at a dose of $4 \times 10^4$ iu/mouse and 1:160 at a dose of $2 \times 10^5$ iu/hamster {the lowest doses tested for each species; (1)}. These studies also indicated that the second-generation RepliVAX was even more potent than the first (1).

Work on a large number of flavivirus vaccine candidates has demonstrated that small animal model potency and efficacy can be predictive of responses in primates. However, in several cases (notably DNA vaccines), lab animal data has not correlated with eventual utility.

To be certain that RepliVAX was a useful platform, a preliminary non-human primate study utilizing the RepliVAX WN.2 vaccine candidate was undertaken. For this study 4 rhesus macaques {seronegative for all commonly circulating flaviviruses (60)} were inoculated with $10^6$ iu of RepliVAX. Evaluation of sera collected from these animals 28 days later revealed 50% NEUT titers (the standard used for non-human primate research) of 1:32 to 1:64, a bit lower than the 50% NEUT titers reported for the YF-17D-based ChimeriVax-WN vaccine (61), a result consistent with the fact that ChimeriVax-WN produced detectable viremia in every monkey included in these published studies (61).

Although the single-dose NEUT titers of the animals were lower than those obtained with live-attenuated virus vaccines capable of producing a viremia, they were similar to those detected in monkeys after receiving two doses of the commercially available Japanese encephalitis virus-inactivated viral vaccine (62). Nevertheless, half of the monkeys were boosted with a second dose of RepliVAX WN.2. Following challenge of these 4 animals and a control, diluent-inoculated macaque with 100,000 pfu of WNV NY99, the animals were tested for viremia on d 1, 2, 4 and 6 post-challenge. The single control animal in this experiment displayed viremias of >100 pfu/ml on d 1, 2, & 4, and a viremia at the limit of detection (7.5 pfu/ml) on d 6. Among the two singly vaccinated animals, one displayed a viremia at the limit of detection (7.5 pfu/ml) on d 1, and all other sera from this animal and all sera from the remaining three vaccinated animals did not display any detectable viremia on any of the other days tested. Thus, this study has clearly documented the efficacy of RepliVAX WN.2 in non-human primates.

Production of an Efficacious RepliVAX JE

By substituting the prM/E genes of Japanese encephalitis virus for the corresponding genes in RepliVAX WN, a chimeric RepliVAX expressing Japanese encephalitis virus SVPs was generated. RepliVAX Japanese encephalitis virus grew poorly in BHK-C* cells, but quickly adapted to grow more rapidly (54). An analogous mutation to those described in 3.2 was detected in the genome of this passaged variant, and this mutation was used to produce a RepliVAX JE.2 which grew to titers of $>10^7$ iu/ml on BHK-C* cells (54). Studies on SVP synthesis from Vero cells infected with parental and 2nd-generation RepliVAX Japanese encephalitis virus indicated that the single mutation in the NS2B/NS3 cleavage site increased the amount of SVPs produced by RepliVAX JE.2 in normal cells (54). Mice and hamsters immunized with RepliVAX JE.2 produced high-titer, Japanese encephalitis virus-specific NEUT titers, and these mice were completely protected from lethal Japanese encephalitis virus challenge (54). There is no suitable Japanese encephalitis virus model for hamsters, so these RepliVAX JE.2-vaccinated hamsters were challenged with West Nile Virus, based on a report demonstrating that an live attenuated virus vaccine for Japanese encephalitis virus could protect hamsters from West Nile encephalitis (WNE) (64). As expected from cross-NEUT titers and anti-NS1 titers, RepliVAX JE.2-vaccinated hamsters were completely protected from lethal West Nile Virus challenge (54).

Cellular Responses to RepliVAX WN

Early (7 d post inoculation) cellular responses of C57/BL6 mice to RepliVAX WN.2 vaccination ($10^4$ or $10^5$ iu) were comparable to those produced by West Nile Virus infection (1,000 pfu). Splenic lymphocytes from the RepliVAX WN-infected animals produced robust CD4 and CD8 T cell cytokine responses following ex-vivo stimulation with synthetic peptides representing dominant WNV-specific epitopes for each type of lymphocyte {Mason & Nikolich-Zugich, OHSU, unpublished and (34)}. RepliVAX WN.2 also elicited a strong CD8 T cell cytotoxic response in these same unpublished studies. These antigen-specific responses were dose-dependent, and RepliVAX WN.2 proved more potent than live West Nile Virus, indicating that RepliVAX WN.2 induced strong antigen-specific T cell responses that likely contribute to its efficacy.

Innate Immune Responses to Single-Cycle Flaviviruses

Mice inoculated with West Nile Virus VRPs (single-cycle particles with the same external structure at RepliVAX—see 3.0 & 3.1) produce large amounts of interferon a (IFN a) as early as 8 h post injection (65), and high levels of interferon a mRNA, replicon RNA, and replicon-encoded antigen were detected in the draining lymph nodes at 24 hour post inoculation (65). Animals inoculated with UV-inactivated VRPs did not produce detectable interferon, indicating that infection was needed to trigger this response.

Since monocyte-derived dendritic cells (mDCs) are likely to be involved as initial targets infectious agents such as RepliVAX, and presentation of its encoded antigens to the adaptive immune system, and plasmacytoid DCs (pDCs) are likely to be involved in production of interferon a (which can modulate adaptive immune responses), studies were performed to test the response of these important cell types to West Nile Virus infection. To this end, pDC and mDC cultures obtained from PBMC of healthy human donors were incubated with WNV for 24 hour, and interferon a in the cell culture supernatants was detected using ELISA.

West Nile Virus elicited the expression of interferon a in both pDC and mDC in a MOI-dependent manner, and pDCs produced about ten-times more interferon a on a per-cell basis than the mDCs. (66). Interestingly, in the case of pDCs, UV-West Nile Virus was equivalent to West Nile Virus in its ability to induce interferon production, whereas in mDCs, UV-West Nile Virus was inactive (66). Effective stimulation of innate immunity is likely important for RepliVAX potency and efficacy, since these responses direct the adaptive immune response; hence interferon induction will be used as a measure for improving RepliVAX. RepliVAX combines many useful aspects of current inactivated viral vaccine and live attenuated virus vaccine technologies, and is hence likely superior to all existing vaccine candidates.

EXAMPLE 2 prM-E-NS1 RepliVAX JE Chimeras in Both RepliVAX YF and RepliVAX WN Genetic Backbones RepliVAX Japanese encephalitis virus chimera built on a RepliVAX WN backbone grew well in BHK-C* cells and protected hamsters from WNE. These RepliVAX-JE-vaccinated hamsters were challenged with West Nile Virus due to lack of a useful hamster model for JE, as a test of the cross-protective immunity raised to JEV. However, RepliVAX JE-elicited immunity to West Nile Virus NS1 (derived from the RepliVAX WN backbone) could have helped to protect against WNE, consistent with previous studies showing that NS1 immunity can provide protection. Therefore, studies were performed to test the role of NS1 immunity in providing protection from WNE in hamsters by comparing VRPs (which express only NS1) with RepliVAX WN.2 (which expresses both West Nile Virus prM/E SVPs and NS1).

These studies demonstrated that RepliVAX WN.2 provided complete protection from both morbidity and mortality, whereas VRPs provided 100% protection from mortality, but failed to keep all hamsters from becoming ill (see Table 1). Although these studies cannot exclude that other aspects of the immune response (notably cellular immunity) help RepliVAX WN to supply superior immunity over VRPs, these data strongly suggest that NS1-specific humoral immunity participates in RepliVAX efficacy.

These studies have two profoundly important implications for chimeric RepliVAX development. First, inclusion of NS1 in a chimera would be expected to produce a better vaccine against the target agent. Second, and equally importantly, this finding indicates that NS1 immunity could interfere with the re-use of chimeric vaccines (since previous immunity to NS1 could interfere with subsequent vaccination with a chimera sharing the NS1 protein present in the first RepliVAX). This same rationale would argue that tetravalent live attenuated virus chimeras could compete with each other following vaccination, producing an "interference" that might help to explain previously reported unequal immune responses to all four serotypes of Dengue virus following a single immunization of a tetravalent dengue live attenuated virus vaccine preparation (containing chimeras) in non-human primates (67). Interference is not a new idea; it has been discussed before in the context of chimeric YF-17D-based vaccines. Interestingly, the possibility that YFV immunity (again likely due to NS1 immunity) could prevent immunization with YF-17D-based chimera expressing DENV2 prM/E, was supported by one non-human primate study (68) but refuted in a human trial (69).

TABLE 1

Vaccination with single-cycle particles expressing only NS1 (VRPs) provides less protection from WNV challenge than RepliVAX WN.[1]

| Vaccine | Dose (IU) | NEUT titer[2] | NS1 ELISA[3] | Mortality[4] | Morbidity[4] |
|---|---|---|---|---|---|
| RepliVAX WN | $2 \times 10^5$ | >1:1280 | 0.50 (.20) | 0 | 0 |
| RepliVAX WN | $4 \times 10^4$ | 1:160 | 0.14 (.10) | 0 | 0 |
| VRP | $1 \times 10^6$ | <1:40 | 0.54 (.21) | 0 | 30 |
| VRP | $2 \times 10^5$ | <1:40 | 0.34 (.19) | 0 | 40 |
| VRP | $4 \times 10^4$ | <1:40 | 0.15 (.08) | 0 | 40 |

[2]90% NEUT titer.
[3]OD values (std. dev.) of NS1 ELISAs.
[4]Morbidity and mortality over 21 d.
[1]10 hamsters per group; ip inoculation; challenge at 21 d.

EXAMPLE 3

Production of an Efficacious TripliVAX JE

To determine the feasibility of adding NS1 from a "foreign" flavivirus to a flavivirus live attenuated virus vaccine, previously described RepliVAX Japanese encephalitis virus live attenuated virus vaccine construct {containing the attenuating, single-cycle phenotype conferred by using a deleted capsid (C) gene} was selected. Addition of NS1 was accomplished by precise fusion of the last codon of NS1 of JEV to the first codon of NS2A of West Nile Virus. Initially, this construct did not replicate well in cell culture (FIG. 4), but upon repeated passage in cells encoding the C gene needed to trans-complement the C-deletion in this NS1-expressing RepliVAX Japanese encephalitis virus chimera (referred to hereon as TripliVAX), produced a TripliVAX with a mutation in the NS4A gene (at position 295 in the NS4A gene) that grew well (FIG. 4). Introduction of this change into the original TripliVAX Japanese encephalitis virus construct confirmed its ability to confer the high-growth phenotype (results not shown).

Testing Efficacy of TripliVAX JE

To test the comparative efficacy of TripliVAX Japanese encephalitis virus (created by passage) and RepliVAX JE, mice were vaccinated with these constructs, bled 21 days later, and then challenged one week later with approximately 30 50%-lethal-doses (LD50) of the Beijing strain of Japanese encephalitis virus. These same studies included groups of mice inoculated with VRPs encoding the original West Nile Virus NS1 protein as well as chimeric West Nile Virus-derived VRPs encoding the Japanese encephalitis virus NS1 protein. Table 3 shows the data obtained from sera collected from these mice 21 days following inoculation.

As expected all constructs encoding the Japanese encephalitis virus NS1 protein produced higher titers of antibodies to NS1. Most remarkable however are the findings that co-expression of the Japanese encephalitis virus NS1 with the Japanese encephalitis virus prM/E cassette resulted in an LAV, which elicited much higher levels of antibodies to the Japanese encephalitis virus E (see shaded areas of Table 2). Most importantly, the enhanced Japanese encephalitis virus E-specific immunity was observed in both the ELISA assay, and in the functionally important neutralization (Neut) assay. In this assay, TripliVAX Japanese encephalitis virus produced much higher Neut titers than RepliVAX Japanese encephalitis virus at both the $1\times10^4$ and $4\times10^4$ doses (Table 2).

When the animals from the experiment shown in Table 3 were challenged with Japanese encephalitis virus, all of the vaccinated groups displayed significantly better protection (p=0.001 by Fisher's exact test using a 2-tailed comparison) than the diluent group (Table 3). TripliVAX Japanese encephalitis virus also appeared to protect better than RepliVAX Japanese encephalitis virus, but these results were not statistically significant with this small number of animals (Table 3). The experiment displayed in Tables 3 and 4 also shows that the JEV NS1 protein, when expressed as part of a VRP, produced higher antibody titers to the NS1 antigen in ELISA (Table 2) and provided better protection from JEV challenge (Table 3).

To obtain additional information on the utility/superiority of TripliVAX Japanese encephalitis virus versus RepliVAX JE, groups of 9 or 10 mice were immunized with lower doses of the two vaccines ($2.5\times10^3$ and $6.25\times10^2$ IU) and challenged with 30 LD50 of Japanese Encephalitis Virus on 4-Week Post Immunization.

As shown in Table 5, 20% and 50% of mice immunized with $2.5\times10^3$ and $6.25\times10^2$ IU of RepliVAX Japanese encephalitis virus died in 21 days, respectively. On the other hand, $2.5\times10^3$ IU of TripliVAX Japanese encephalitis virus provided 100% protection and $6.25\times10^2$ IU of TripliVAX Japanese encephalitis virus produced 90% protection from death. For all four of these vaccinated groups, all of the mice that survived did not show any measurable manifestations of JEV-induced disease, and none of the surviving mice displayed a challenge-induced weight loss (Table 5). On the other hand, a large fraction (3 out of 9) of the mice that were given diluent and survived infection displayed considerable weight loss in the challenge period (Table 5).

Thus, TripliVAX Japanese encephalitis virus is a better vaccine than RepliVAX Japanese encephalitis virus based on antibodies it elicits to E, antibodies it elicits to NS1, and efficacy data in a mouse model for Japanese encephalitis virus. By extension, addition of NS1 to any type of chimeric live attenuated virus vaccine would be expected to improve its potency and efficacy.

TABLE 2

TripliVAX JE induced superior immune responses to RepliVAX JE.

| Vaccine | Dose (iu) | JEV Neut titer[a] | ELISA titer[b] JEV E | JEV NS1 | WNV NS1 |
|---|---|---|---|---|---|
| RepliVAX JE | $4\times10^4$ | 1:80 | 1:800 | 1:200 | 1:800 |
| RepliVAX JE | $1\times10^4$ | 1:80 | 1:800 | <1:100 | 1:800 |
| RepliVAX JE | $2.5\times10^3$ | 1:80 | 1:400 | <1:100 | 1:800 |
| TripliVAX JE | $4\times10^4$ | 1:320 | >1:6400 | 1:200 | <1:100 |
| TripliVAX JE | $1\times10^4$ | 1:160 | 1:6400 | 1:100 | <1:100 |
| TripliVAX JE | $2.5\times10^3$ | 1:80 | 1:1600 | 1:100 | <1:100 |
| diluent | — | <1:40 | — | — | — |
| VRP | $1\times10^6$ | <1:40 | <1:100 | 1:100 | 1:3200 |
| VRP-JENS1 | $1\times10^6$ | <1:40 | <1:100 | 1:400 | <1:100 |

[a]90% PRNT specific for JEV was determined with a Luc gene-expressing VRP coated with JEV E protein.
[b]ELISA titers are maximum dilution factors whose OD were greater than OD + 3S.D. obtained from the diluent group.

TABLE 3

Comparison of role of JE NS1 in improving protective potential of RepliVAX JE and VRPs against JEV-induced mortality.

| Immunogen | Dose (iu) | Mortality (%)[a] |
|---|---|---|
| RepliVAX JE | $4\times10^4$ | 10% |
| RepliVAX JE | $1\times10^4$ | 10% |
| RepliVAX JE | $2.5\times10^3$ | 10% |
| TripliVAX JE | $4\times10^4$ | 0% |
| TripliVAX JE | $1\times10^4$ | 0% |
| TripliVAX JE | $2.5\times10^3$ | 10% |
| diluent | — | 90% |
| VRP | $1\times10^6$ | 60% |
| VRP-JE NS1 | $1\times10^6$ | 20% |

[a]Mice vaccinated with the indicated vaccines were challenged with 30LD$_{50}$ of JEV 4 weeks post vaccination and observed for 21 days.

TABLE 4

RepliVAX JE trimeras produce superior immune responses to RepliVAX JE chimeras.

| Vaccine (based on RepliVAX WN LAV) | Vaccine Dose (iu) | ELISA titer JEV E | JEV NS1 | WNV NS1 |
|---|---|---|---|---|
| JE chimera | $4\times10^4$ | 1:800 | 1:200 | 1:800 |
| JE chimera | $1\times10^4$ | 1:800 | <1:100 | 1:800 |
| JE chimera | $2.5\times10^3$ | 1:400 | <1:100 | 1:800 |
| JE trimera | $4\times10^4$ | >1:6400 | 1:200 | <1:100 |
| JE trimera | $1\times10^4$ | 1:6400 | 1:100 | <1:100 |
| JE trimera | $2.5\times10^3$ | 1:1600 | 1:100 | <1:100 |
| diluent | — | — | — | — |

TABLE 5

RepliVAX JE trimeras provide superior protection from death and disease than RepliVAX JE chimeras.

| Vaccine (based on RepliVAX WN LAV) | Vaccine Dose (IU) | Percent Mortality (#/group)[a] | Percent Morbidity (%)[b] |
|---|---|---|---|
| JE chimera | $2.5\times10^3$ | 20 (2/10) | 20 (2/10) |
| JE chimera | $6.25\times10^2$ | 50 (5/10) | 50 (5/10) |
| JE trimera | $2.5\times10^3$ | 0 (0/10) | 0 (0/10) |
| JE trimera | $6.25\times10^2$ | 10 (1/10) | 10 (1/10) |
| diluent | — | 45 (4/9) | 78 (7/9) |

[a]Mortality in these groups indicate the % of mice that died in the 21-day observation period that followed challenge with 30LD$_{50}$ of JEV 4 weeks post vaccination.
[b]Morbidity indicates the sum of animals that died during the 21-day observation period and the animals that displayed a loss in weight of at least 20% during the observation period.

EXAMPLE 4

Improving TripliVAX JE by Accumulation of Adaptive Mutations that Occurred in Multiple Passages As described above, the anti-NS immunity conferred by single-cycle flaviviruses can protect animals from lethal flavivirus challenge. Since a portion of this immunity was likely due to the NS1 protein, it was reasoned that incorporation of NS1 into a chimeric LAV, such as RepliVAX, would make the vaccine more effective. Prior to construction of a prM/E/NS1 chimeric RepliVAX JE, a prM/E/NS1 chimeric live virus named Trimera JE was prepared in order to assess the replicational competence of prM/E/NS1 chimerization without the complicating factor of C-transcomplementation required for propagation of RepliVAX chimeras.

Initially, the Trimera JE RNA was introduced into BHK (VEErep/Pac-Ubi-WNNS1NS2A) cells expressing WNV NS1 as well as wild-type BHK cells. Progeny Trimera JE was recovered from both cell lines (data not shown), indicating that trans-complementation with the authentic WNV NS1 was not essential for propagation of this Trimera JE. Based on this result, wild-type BHK cells were used in all subsequent experiments using Trimera JE, to simplify the manipulations. Initially Trimera JE grew poorly and produced small foci on BHK cells, but following 14 sequential passages, a derivative population of Trimera JE capable of producing larger foci was obtained. Sequence analyses revealed that the blind-passed Trimera JE population contained four amino acid changes in C, prM and NS4A genes (Table 6).

Once it was confirmed that prM/E/NS1 chimerization was not lethal in the context of an intact viral genome, we constructed a prM/E/NS1 chimeric single-cycle JE vaccine, which we named TripliVAX JE, by replacing the WNV NS1 gene of RepliVAX JE with the JEV NS1 gene. When introduced into BHK(VEErep/Pac-Ubi-C*) cells, TripliVAX JE displayed small foci, similar to the foci observed with Trimera JE on wild-type BHK cells (FIG. 6). To obtain a better-growing derivative of this single-cycle virus, TripliVAX JE was blind-passed in BHK(VEErep/Pac-Ubi-C*) cells. Following 15 blind-passages, a TripliVAX JE population capable of producing larger foci was obtained (FIG. 6B). To further characterize the phenotype of these viruses, the numbers of cells forming individual foci were counted. The foci of un-passaged TripliVAX JE (p0) contained 15.8±8.8 (n=15 foci) cells, while those of blind-passed TripliVAX JE (p15) contained significantly larger number of cells (47.1±19.9; n=15 foci; p<0.001). This better-growing TripliVAX JE had a mutation (V29I in NS4A) identical to that found in Trimera JE (Table 6), suggesting that the V29I mutation in NS4A was responsible for the growth improvement of both types of prM/E/NS1 chimeric constructs.

Examination of the Effects of the NS4A Mutation in Trimera JE and TripliVAX JE on Their Growth In order to examine the effects of the NS4A mutation found in blind-passed Trimera JE and TripliVAX JE, the V29I mutation was introduced into the parental Trimera JE and TripliVAX JE, producing new variants designated as Trimera JE-NS4A* and TripliVAX JE-NS4A*, respectively.

Consistent with the passaged versions of the original constructs described above, Trimera JE-NS4A* produced foci that were larger than the parental Trimera JE and similar to those produced by blind-passed Trimera JE (FIG. 6A). As expected, Trimera JE-NS4A* grew better than parental Trimera JE and its growth kinetic was similar to that of blind-passed Trimera JE (FIG. 7A). Thus, this NS4A mutation was responsible for the growth improvement of the passaged derivative of Trimera JE.

Similar examinations were performed using TripliVAX JE-NS4A*. The foci produced by TripliVAX JE-NS4A* on BHK(VEErep/Pac-Ubi-C*) cells were larger than parental TripliVAX JE (FIG. 6B) and the mean number of cells forming a focus (45.8±23.7) was similar to those of blind-passed TripliVAX JE. However, side-by-side growth curves of TripliVAX JE-NS4A* and its parental TripliVAX JE, demonstrated that the new construct did not reach the titers obtained with the blind-passed TripliVAX JE (FIG. 7B). These results suggested that an additional mutation in the highly passaged TripliVAX JE (possibly the other substitution in NS4A (G18R)) could be responsible, in part, for the higher growth rate of the passage-15 TripliVAX JE.

To determine if the V29I substitution altered the growth properties of RepliVAX JE and RepliVAX WN, RepliVAX JE-NS4A* and RepliVAX WN-NS4A* were constructed. By contrast to the effects of the mutation observed in Trimera JE and TripliVAX JE, RepliVAX JE-NS4A* and RepliVAX WN-NS4A* exhibited identical growth kinetics to those of the parent RepliVAX JE and RepliVAX WN, respectively (data not shown). Taken together, these data suggest that the growth improving properties of the V29I substitution in NS4A were only evident in chimeric viruses that encoded both the NS1 and prM/E cassettes of JEV.

TABLE 6

Sequence analysis of blind-passaged Trimera JE and TripliVAX JE.

| Construct | Region | Position[a] | Amino Acid change |
|---|---|---|---|
| Trimera JE | C | 62 | T to S |
| | prM | 47 | D to N |
| | NS4A | 29 | V to I |
| | NS4A | 135 | V to M |
| TripliVAX JE | NS4A | 18 | G to R, G to G |
| | NS4A | 29 | V to I |

[a]position in each viral protein is indicated.

Examination of the Effects of the NS4A Mutation in Trimera JE and TripliVAX JE on Their Growth.

In order to examine the effects of the NS4A mutation found in blind-passed Trimera JE and TripliVAX JE, the V29I mutation was introduced into the parental Trimera JE and TripliVAX JE, producing new variants designated as Trimera JE-NS4A* and TripliVAX JE-NS4A*, respectively.

Consistent with the passaged versions of the original constructs described above, Trimera JE-NS4A* produced foci that were larger than the parental Trimera JE and similar to those produced by blind-passed Trimera JE (FIG. 6A). As expected, Trimera JE-NS4A* grew better than parental Trimera JE and its growth kinetic was similar to that of blind-passed Trimera JE (FIG. 7A). Thus, this NS4A mutation was responsible for the growth improvement of the passaged derivative of Trimera JE.

Similar examinations were performed using TripliVAX JE-NS4A*. The foci produced by TripliVAX JE-NS4A* on BHK(VEErep/Pac-Ubi-C*) cells were larger than parental TripliVAX JE (FIG. 6B) and the mean number of cells forming a focus (45.8±23.7) was similar to those of blind-passed TripliVAX JE. Growth curves of TripliVAX JE-NS4A* revealed more growth compared to its parental TripliVAX JE, although TripliVAX JE-NS4A* did not reach the titers obtained with the blind-passed TripliVAX JE (FIG. 7B). These results suggested that an additional mutation in the highly passaged TripliVAX JE (possibly the other substitution in NS4A (G18R)) could be responsible, in part, for the higher growth rate of the passage-15 TripliVAX JE.

Evaluation of Blind-Passed TripliVAX JE in Mice

To evaluate TripliVAX JE as a vaccine candidate in animal models, immunogenicity and protective efficacy of TripliVAX JE were compared to RepliVAX JE. In this experiment, blind-passed TripliVAX JE which contained mutations in NS4A was used.

Figures 8A, 8B:
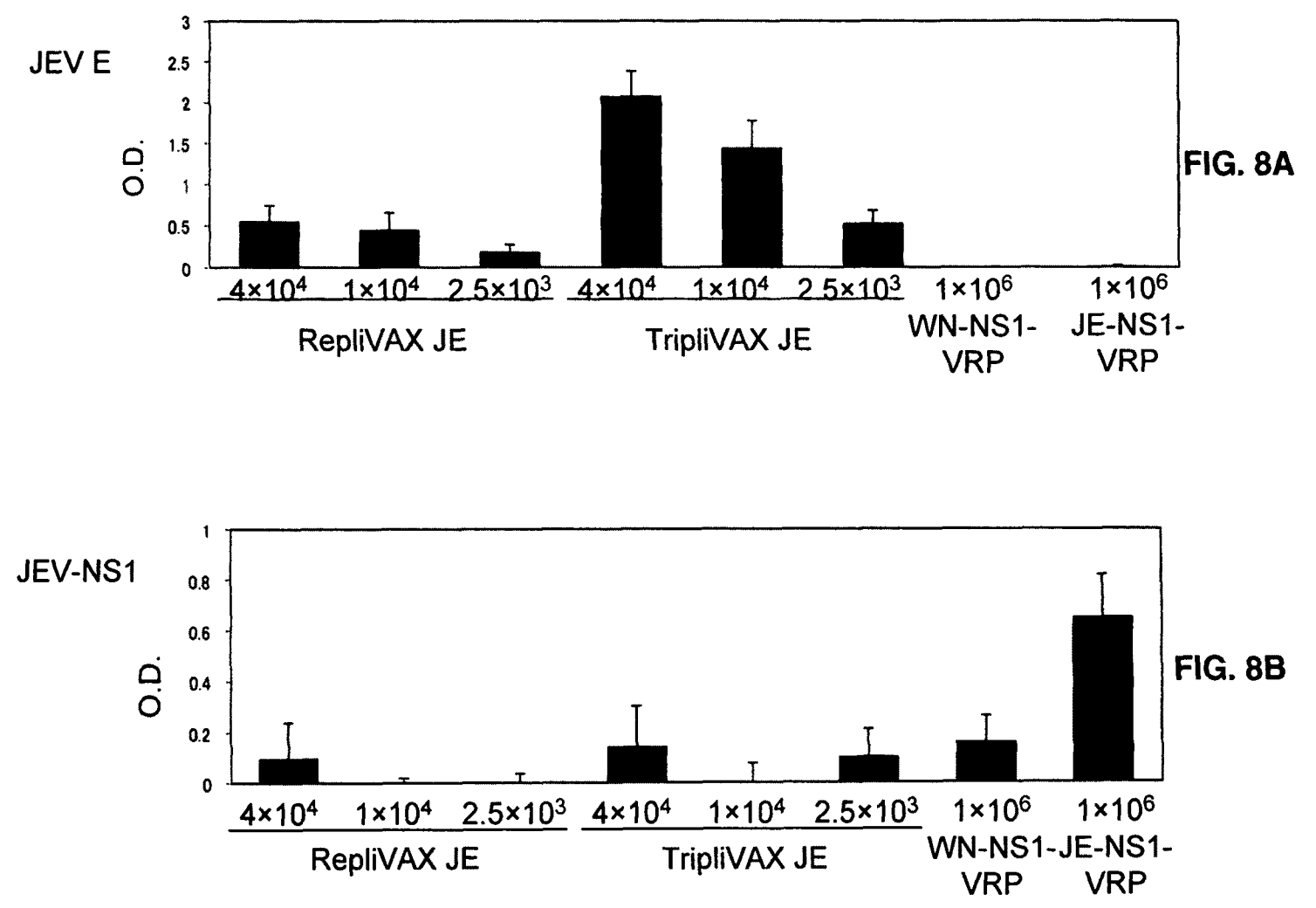
Figure 8C:
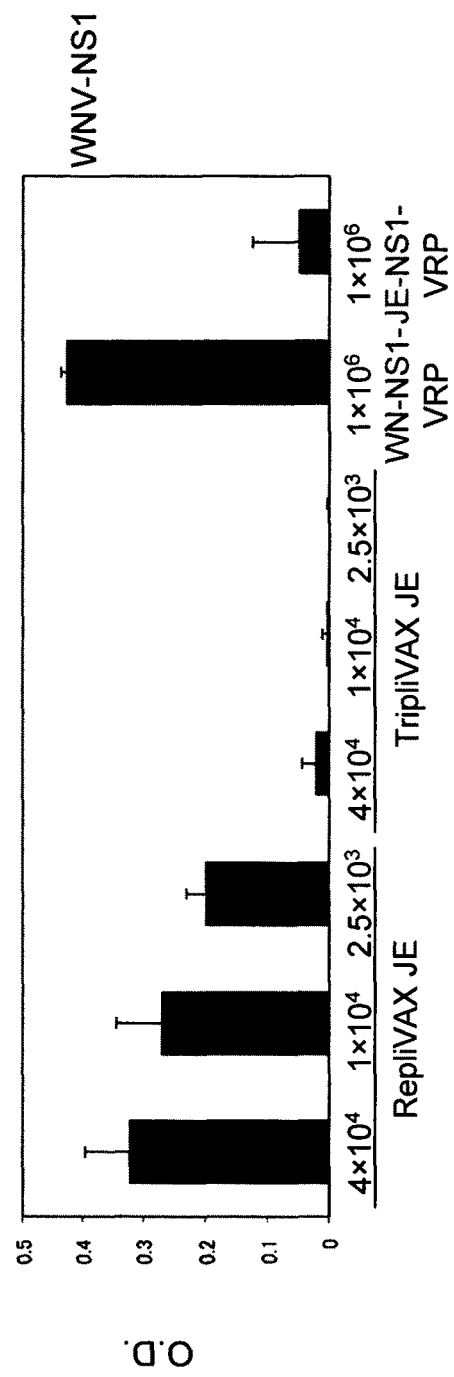
FIG. 8. Comparison of immune responses induced by TripliVAX JE and RepliVAX JE. Panel shows mouse serum IgG antibody responses against JEV E (8A), JEV NS1 (8B) and WNV NS1 (8C) 21 days post-immunization. Bars represent the group average O.D. and extended bars show SD. The average O.D. obtained from media control (L15)-immunized group was subtracted from those of other groups.

At 21 days post-immunization, all mice immunized with either TripliVAX JE or RepliVAX JE elicited detectable neutralizing antibodies (Table 7). All three groups immunized with TripliVAX JE developed higher neutralizing antibody titers than groups immunized with similar doses of RepliVAX JE (Table 7). As expected, mice immunized with either JE-NS1-VRPs or WN-NS1-VRPs failed to develop detectable neutralizing antibodies. Antibody levels against JEV E, JEV NS1 and WNV NS1 were also assessed by ELISA using individual sera. As expected from the neutralization data in Table 7, TripliVAX JE-immunized mice showed higher levels of anti-JEV E antibodies than RepliVAX JE at all three doses tested (FIG. 8). Again, as expected from the neutralization data in Table 7, almost no immune responses against JEV E were detected in JE-NS1-VRP- and WN-NS1-VRP-immunized groups. Unexpectedly, equivalent levels of antibody responses against JEV NS1 were observed both in TripliVAX JE- and RepliVAX JE-immunized groups, although JE-NS1-VRP-immunized mice developed higher anti-JEV NS1 immune responses than WN-NS1-VRP-immunized mice (FIG. 8). On the other hand, RepliVAX JE-immunized mice developed significantly higher anti-WNV NS1 immune responses than TripliVAX JE-immunized mice (FIG. 8). Almost no immune responses against WNV NS1 were observed in TripliVAX JE-immunized groups. WN-NS1-VRP-immunized mice showed higher immune responses against WNV NS1 than JE-NS1-VRP-immunized mice. These results suggested that TripliVAX JE is a superior vaccine candidate to RepliVAX JE, since it induced better anti-E immune responses, although levels of antibodies to JEV NS1 were comparable.

To compare protective efficacy of TripliVAX JE and RepliVAX JE, the mice were challenged with 30 $LD_{50}$ of JEV Beijing P3 strain at 28 days post-immunization. More than 90% of mice immunized with either TripliVAX JE or RepliVAX JE survived the challenge. Single doses of $4 \times 10^4$ or $1 \times 10^4$ IU of TripliVAX JE provided 100% protection, whereas $4 \times 10^4$ or $1 \times 10^4$ IU of RepliVAX JE provided 90% protection. Both $2.5 \times 10^3$ IU of TripliVAX JE and RepliVAX JE showed 90% protection (Table 7). There were no significant differences in mortality or morbidity between groups immunized with TripliVAX JE and RepliVAX JE. When both VRP-immunized groups were compared, JE-NS1-VRP immunization provided 80% protection (20% morbidity), while WN-NS1-VRP immunization provided only 22% protection (78% morbidity) (Table 7). These results showed again the contribution of anti-NS immunity (in particular NS1) to the protection animals from JEV disease.

TABLE 7

Comparison of TripliVAX JE and RepliVAX JE

| Immunogen | Dose (IU) | Neut titer[a] | Mortality (%) | Morbidity (%)[b] |
|---|---|---|---|---|
| RepliVAX JE | 4_10$^4$ | 90 | 10 | 10 |
| RepliVAX JE | 1_10$^4$ | 86 | 10 | 20 |
| RepliVAX JE | 2.5_10$^3$ | 69 | 10 | 10 |

TABLE 7-continued

Comparison of TripliVAX JE and RepliVAX JE

| Immunogen | Dose (IU) | Neut titer[a] | Mortality (%) | Morbidity (%)[b] |
|---|---|---|---|---|
| TripliVAX JE | 4_10$^4$ | 446 | 0 | 0 |
| TripliVAX JE | 1_10$^4$ | 308 | 0 | 10 |
| TripliVAX JE | 2.5_10$^3$ | 147 | 10 | 20 |
| L15 | — | <40 | 89 | 100 |
| WN-NS1-VRP | 1_10$^6$ | <40 | 56 | 78 |
| JE-NS1-VRP | 1_10$^6$ | <40 | 20 | 20 |

[a]90% luciferase activity reduction neutralizing antibody titers were determined at 21 days post-immunization.
[b]Weight loss of >10% was scored as JEV-induced morbidity.

Examination of Blind-Passed TripliVAX JE with Low-Dose Regimen

To further evaluate the potential superiority of TripliVAX JE as a vaccine to prevent JE, a lower dose regimen of RepliVAX JE and TripliVAX was utilized. To this end, mice were immunized once with $2.5 \times 10^3$ or $6.25 \times 10^2$ IU of TripliVAX JE or RepliVAX JE. Interestingly, even this very low-dose immunization induced detectable neutralizing antibody titers (46 to 99), but there were no significant differences in neutralization titers detected between the responses to this low dose of TripliVAX JE and RepliVAX JE at 21 days post-immunization (Table 5). In accordance with the serological data obtained from the evaluation of a high dose regimen described above, $2.5 \times 10^3$ IU of TripliVAX JE-immunized mice induced higher anti-E and anti-JEV NS1 immune responses than RepliVAX JE-immunized mice (FIG. 9). To evaluate efficacy, these mice were challenged with 30 $LD_{50}$ of JEV Beijing P3 strain at 28 days post-immunization. Mice immunized with $2.5 \times 10^3$ IU of TripliVAX JE exhibited 100% protection (0% mortality) and mice immunized with $6.25 \times 10^2$ IU of TripliVAX JE exhibited 90% protection (10% mortality) (Table 5). In contrast, mice immunized with $2.5 \times 10^3$ IU of RepliVAX JE exhibited 80% protection (20% mortality) and mice immunized with $6.25 \times 10^2$ IU of RepliVAX JE exhibited only 50% protection (50% mortality). Although the differences in protection between these groups were not significant, the trend between them supported the contention that TripliVAX JE is a superior vaccine to RepliVAX JE.

EXAMPLE 5

TripliVAX JE Displayed Reduced Immune Interference Caused by Pre-Existing Anti-NS1 Immunity As described above, anti-NS1 immunity plays an important role in flavivirus protection. This fact raised a concern that pre-existing anti-NS1 immunity could result in immune interference. Since many chimeric flavivirus vaccines in development have utilized prM/E chimerization strategy, and thus share the same nonstructural protein backbone (including NS1), anti-NS1 immunity induced by either infection or immunization could interfere with subsequent immune responses induced by a vaccine sharing the same NS1. In these cases, prM/E/NS1 chimerization utilized in TripliVAX JE could reduce interference with vaccine potency/efficacy.

To test this hypothesis, mice were immunized with WN-NS1-VRP to provide an initial vaccination that elicited a strong NS1-specific immunity in the absence of any significant anti-E immune responses. At 20 days post-vaccination immune responses against WNV NS1 were seen in this group, but no detectable immune responses against JEV E were observed, whereas control, mice (inoculated with L15 media only) did not display any responses to either antigen (data not shown). At 21 days post-immunization, all mice were then vaccinated with either 4×10⁴ IU of TripliVAX JE or RepliVAX JE. Twenty one days later (42 days post first vaccination), sera were collected and serological analyses were conducted.

Animals immunized first with L15 media followed by TripliVAX JE or RepliVAX JE, developed good JEV E-specific ELISA antibody responses with group titers of 6580 and 4651, respectively (Table 8). Pre-existing NS1 immunity (produced by initial immunization with WN-NS1-VRPs), reduced the JEV E-specific antibody responses elicited by either TripliVAX JE or RepliVAX JE (Table 8). However the titer in TripliVAX JE-immunized animals was 3408 which represented only a 48% reduction in titer compared to that in animals immunized first with L15, whereas in RepliVAX JE-immunized mice the titer was 1150 which represented a 75% reduction in ELISA antibody titer relative to that achieved in the group that was immunized first with L15 media.

Figures 10A, 10B:
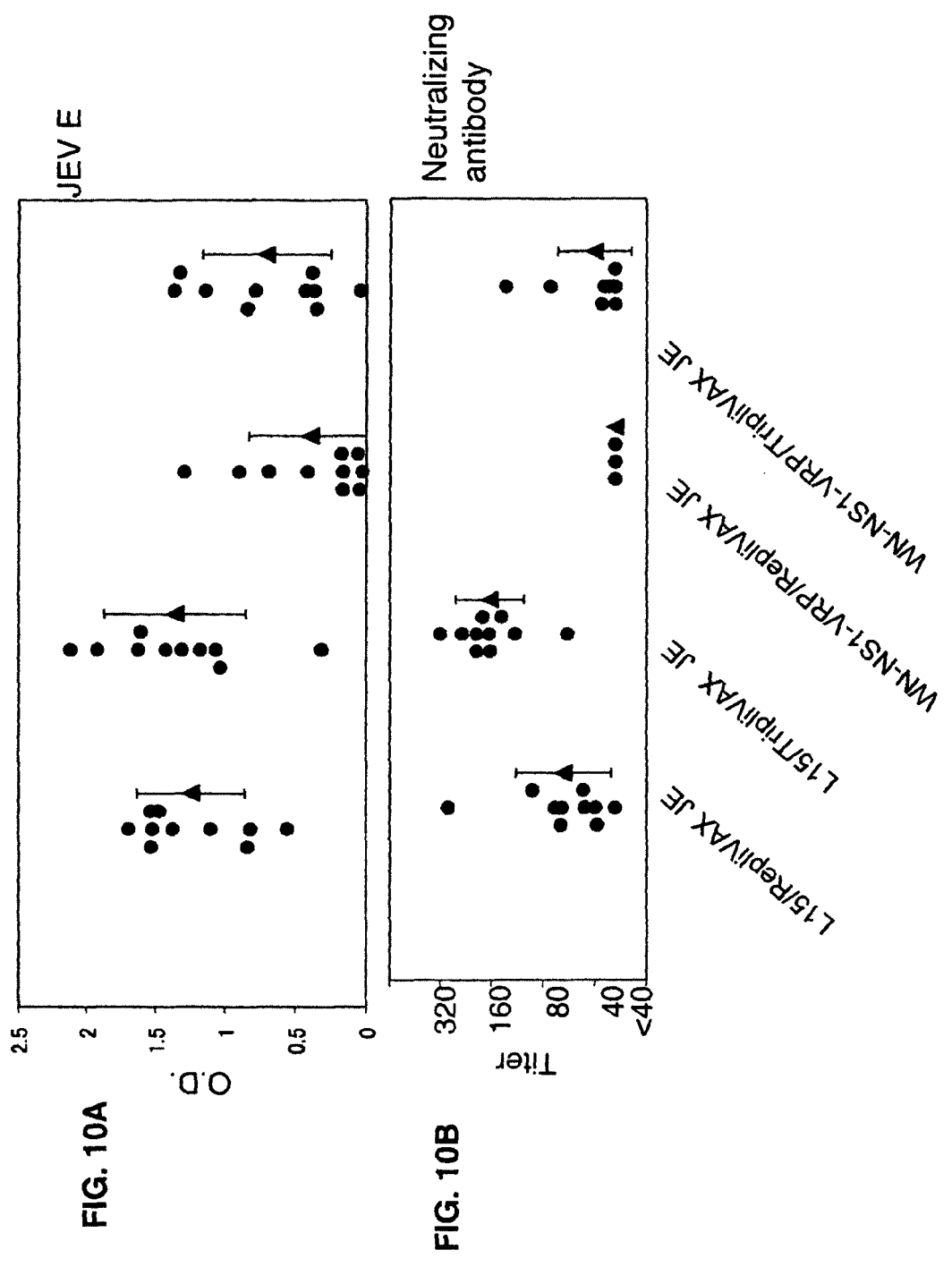

Comparison of the ELISA antibody levels found in individual animals in these groups revealed that both groups that were first immunized with WN-NS1-VRPs exhibited lower JE E-specific immune responses relative to both groups of animals that were inoculated with L15 (FIG. 10). However, the ELISA antibody levels of the groups of mice that were immunized first with WN-NS1-VRPs revealed that a preponderance of animals then vaccinated with RepliVAX JE demonstrated barely detectable anti-E responses (p=0.0002; vs animals immunized with RepliVAX JE in the absence of WN-NS1-VRPs), whereas nearly all animals first immunized with WN-NS1-VRPs and then immunized with TripliVAX JE had more robust anti-E responses, with many reaching antibody levels comparable to those observed in non-primed animals (p=0.0074; vs animals immunized with TripliVAX JE in the absence of WN-NS1-VRPs). These results demonstrate that previous immunization with WN-NS1-VRPs reduced the potency of TripliVAX JE to a lesser extent than it reduced the potency of RepliVAX JE. The superiority TripliVAX JE over RepliVax JE in overcoming pre-existing NS-1 immunity was further illustrated by examination of the neutralizing antibody titers (Table 8). In the absence of a WN-NS1-VRP immunization, TripliVAX JE and RepliVAX JE elicited neutralizing antibody titers of 155 and 120, respectively. However, mice given WN-NS1-VRPs and then immunized with TripliVAX JE developed a 121 neutralizing antibody titer, whereas mice given WN-NS1-VRPs and then immunized with RepliVAX JE only developed a 71 neutralizing antibody titer. A side-by-side repeat comparison of the ability of these pooled sera to neutralize JELucVRPs confirmed the superior potency of the TripliVAX JE relative to RepliVAX JE in animals that had high-titer antibodies to the WNV NS1 (data not shown). To further confirm these trends, neutralizing antibody titers were measured in individual sera obtained from these animals (FIG. 10B). As described above for the individual ELISA data (FIG. 10A) and ELISA titers and neutralization titers obtained with pooled sera (Table 8), mice given WN-NS1-VRPs and then immunized with TripliVAX JE exhibited higher neutralizing antibody titers than mice given WN-NS1-VRPs and then immunized with RepliVAX JE, although some immune interference was observed in both groups (FIG. 10B). Taken together, these results indicate that TripliVAX JE is less susceptible interference caused by pre-existing WNV-specific anti-NS1 immunity than the traditional type of prM/E LAV chimera represented here by RepliVAX JE.

TABLE 8

Effects of pre-existing anti-NS1 immunity on immunization with RepliVAX JE and TripliVAX JE

| Immunogen (1st/2nd) | Dose (IU) (1st/2nd) | Neut titer[a] | Anti-E ELISA titer[b] |
|---|---|---|---|
| L15/RepliVAX JE | —/4_10⁴ | 120 | 4651 |
| L15/TripliVAX JE | —/4_10⁴ | 155 | 6580 |
| WN-NS1-VRP/RepliVAX JE | 1_10⁶/4_10⁴ | 71 | 1150 |
| WN-NS1-VRP/TripliVAX JE | 1_10⁶/4_10⁴ | 121 | 3408 |

[a]90% luciferase activity reduction neutralizing antibody titers were determined at 21 days post-2nd immunization.
[b]Titers were expressed as the maximum reciprocal serum dilution showing absorbance greater than absorbance obtained with control mouse sera at 1:100 (Av + 3SD) against JEV E protein.

The following references are cited herein:
1. Widman, D. G., T. Ishikawa, et al. 2008. Vaccine 26:2762-2771.
2. Oya, A., and I. Kurane. 2007. J Travel Med 14:259-68
3. CDC. 2008. Chapter 4: Prevention of Specific Infectious Diseases—Japanese Encephalitis, Travelers' Health: Yellow Book.
4. Hayes, E. B. 2007. Trans R Soc Trop Med Hyg 101:967-71
5. WHO. 1976. WHO Expert Committee on Biological Standardization. Twenty-seventh report. World Health Organ Tech Rep Ser: 23-49
6. WHO. 1998. WHO Expert Committee on Biological Standardization. Forty-sixth Report. World Health Organ Tech Rep Ser 872:i-vii, 1-90
7. WHO. 2000. Dengue/dengue haemorrhagic fever. Weekly Epidemiological Record 75:193-196
8. Halstead, S. B., and J. Deen. 2002. Lancet 360:1243-5
9. Mason, P. W., S. Pincus, et al. 1991. Virology 180:294-305.
10. Konishi, E., S. Pincus, et al. 1992. Virology 188:714-20.
11. Pincus, S., P. W. Mason, et al. 1992. Virology 187:290-7.
12. Fonseca, B. A., S. Pincus, et al. 1994. Vaccine 12:279-85
13. Aberle, J. H., S. W. Aberle, et al. 1999. J Immunol 163:6756-61
14. Qiao, M., M. Ashok, et al. 2004. J Infect Dis 190:2104-8
15. Tauber, E., H. Kollaritsch, et al. 2007. Lancet 370:1847-53
16. Watts, D. M., R. B. Tesh, et al. 2007. Vaccine 25:2913-8
17. Lieberman, M. M., D. E. Clements, et al. 2007. Vaccine 25:414-23
18. White, L. J., M. M. Parsons, et al. 2007. J Virol 81:10329-39
19. Davis, N. L., I. J. Caley, et al. 2000. J Virol 74:371-8
20. Kanesa-thasan, N., J. J. Smucny, et al. 2000. Vaccine 19:483-491
21. Martin, J. E., T. C. Pierson, et al. 2007. J Infect Dis 196:1732-40
22. Kuhn, R. J., W. Zhang, et al. 2002. Cell 108:717-725
23. Lindenbach, B. D., and C. M. Rice. 2007. Flaviviridae: The viruses and their replication. In B. N. Fields, D. M. Knipe, and P. M. Howley (ed.), Fields Virology, 5th ed. Wolters Kluwer Health/Lippincott Williams & Wilkins, Philadelphia.
24. Schlesinger, J. J., M. W. Brandriss et al. 1985. J Immunol 135:2805-9
25. Konishi, E., S. Pincus, et al. 1991. Virology 185:401-10.
26. Chung, K. M., G. E. Nybakken, et al. 2006. J Virol 80:1340-51
27. Engle, M. J., and M. S. Diamond. 2003. J Virol 77:12941-9

28. Diamond, M. S., B. Shrestha, et al. 2003. J Virol 77:2578-86
29. Charlier, N., et al. 2002. J Gen Virol 83:1887-96
30. Halevy, M., Y. Akov, et al. 1994. Arch Virol 137:355-70
31. Murali-Krishna, K., V. Ravi, et al. 1996. J Gen Virol 77:705-14
32. Wang, Y., M. Lobigs, et al. 2003. J Virol 77:13323-34
33. Shrestha, B., and M. S. Diamond. 2004. J Virol 78:8312-21
34. Brien, J. D., J. L. Uhrlaub, et al. 2007. Eur J Immunol 37:1855-63
35. Purtha, W. E., N. Myers, et al. 2007. Eur J Immunol 37:1845-54
36. Sitati, E. M., and M. S. Diamond. 2006. J Virol 80:12060-9
37. Konishi, E., I. Kurane, et al. 1998. Vaccine 16:842-9.
38. Gardner, I. D. 1980. Rev Infect Dis 2:801-10
39. Hahn, C. S., Y. S. Hahn, et al. 1987. J Mol Biol 198:33-41
40. Khromykh, A. A., H. Meka, et al. 2001. Journal of Virology 75:6719-6728
41. Corver, J., E. Lenches, et al. 2003. J Virol 77:2265-70
42. Khromykh, A. A., and E. G. Westaway. 1997. J Virol 71:1497-505
43. Pang, X., M. Zhang, and A. I. Dayton. 2001. BMC Microbiol 1:18
44. Gehrke, R., M. Ecker, et al. 2003. J Virol 77:8924-33
45. Lo, M. K., M. Tilgner, K. A. Bernard, and P. Shi. 2003. J Virol 77:10004-14
46. Rossi, S. L., Q. Zhao, et al. 2005. Virology 331:457-70
47. Jones, C. T., C. G. Patkar, and R. J. Kuhn. 2005. Virology 331:247-59
48. Harvey, T. J., W. J. Liu, et al. 2004. J Virol 78:531-8
49. Scholle, F., Y. A. Girard, et al. 2004. J Virol 78:11605-14
50. Hanna, S. L., T. C. Pierson, et al. 2005. J Virol 79:13262-74
51. Pierson, T. C., M. D. Sanchez, et al. 2006. Virology 346:53-65
52. Fayzulin, R., F. Scholle, et al. 2006. Virology 351:196-209 16647099.
53. Mason, P. W., A. V. Shustov, et al. 2006. Virology 351:432-443 16712897.
54. Ishikawa, T., D. G. Widman, et al. 2008. Vaccine 26:2772-2781 18433947.
55. Petrakova, O., E. Volkova, et al. 2005. J Virol 79:7597-608
56. Yamshchikov, V. F., D. Trent, and R. Compans. 1997. J Virol 71:4364-71
57. Lee, E., C. E. Stocks, et al. 2000. Journal of Virology 74:24-32
58. Lobigs, M., and E. Lee. 2004. J Virol 78:178-86
59. Keelapang, P., R. Sriburi, et al. 2004. J Virol 78:2367-81
60. Ratterree, M. S., R. A. Gutierrez, et al. 2004. J Infect Dis 189:669-76
61. Arroyo, J., C. Miller, et al 2004. J Virol 78:12497-507
62. Raengsakulrach, B., A. Nisalak, et al. 1999. Am J Trop Med Hyg 60:343-9
63. Guirakhoo, F., J. Arroyo, et al. 2001. Journal of Virology 75:7290-7304
64. Tesh, R. B., A. Travassos da Rosa, et al. 2002. Emerg Infect Dis 8:245-51
65. Bourne, N., F. Scholle, et al. 2007. J Virol 81:9100-8 17567689.
66. Silva, M. C., A. Guerrero-Plata, et al. 2007. J Virol: 13640-8 17913823.
67. Blaney, J. E., Jr., J. M. Matro, et al. 2005. J Virol 79:5516-28
68. Galler, R., R. S. Marchevsky, et al. 2005. Braz J Med Biol Res 38:1835-46
69. Guirakhoo, F., S. Kitchener, et al. 2006. Hum Vaccin 2:60-7
70. Lindenbach, B. D., and C. M. Rice. 1999. J Virol 73:4611-21
71. Junt, T., E. A. Moseman, M. Iannacone, et al. 2007. Nature 450:110-4
72. Gilfoy, F. D., and P. W. Mason. 2007. J Virol 81:11148-11158
73. Monath, T. 2004. Yellow fever vaccine, p. 1095-1176. In S. Plotkin and W. A. Orenstein (ed.), Vaccine, 5th ed. W.B. Saunders Company, Philadelphia, Pa.
74. Levenbook, I. S., L. Pelleu, and B. Elisberg. 1987. J Biol Stand 15:305-13
75. 1998. WHO Expert Committee on Biological Standardization. Forty-sixth Report. World Health Organ Tech Rep Ser 872:1-vii, 1-90
76. Monath, T. P., I. Levenbook, et al. 2000. Journal of Virology 74:1742-1751
77. Raengsakulrach, B., Nisalak, et al. 1999. Am J Trop Med Hyg 60:329-37
78. Sariol, C., J. Munoz-Jordan, et al. 2007. Clin Vaccine Immunol 14:756-66
79. Ratterree, M. S., A. P. da Rosa, et al. 2003. Emerg Infect Dis 9:1388-94
80. Pogodina, V. V., M. P. Frolova, et al. 1983. Arch Virol 75:71-86
81. Shustov, A., P. W. Mason, et al. 2007. J Virol 81:11737-11748 17715227.
82. McArthur, M. A., M. T. Suderman, et al. 2003. J Virol 77:1462-8
83. McGee, C. E., M. G. Lewis, et al. 2008. J Infect Dis
84. Guirakhoo, F., K. Pugachev, et al. 2004. J Virol 78:4761-75
85. Kaufman, B., P. L. Summers, et al. 1987. Am J Trop Med Hyg 36:427-34
86. Caufour, P. S., M. C. A. Motta, et al. 2001. Virus Research 79:1-14
87. Johnson, A. J., and J. T. Roehrig. 1999. J Virol 73:783-6
88. Huang, C. Y., S. Butrapet, et al. 2003. J Virol 77:11436-47
89. Calvert, A. E., C. Y. Huang, et al. 2006. J Gen Virol 87:339-46
90. Schul, W., W. Liu, et al. 2007. J Infect Dis 195:665-74
91. Vaughn, D., et al. 2000. Journal of Infectious Diseases. Jan. 181:2-9

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A live-attenuated trimeric flavivirus, comprising:
   a first flavivirus encoding a membrane precursor gene (prM), envelope gene (E) and a NS1 gene (NS1) from a second flavivirus, wherein said first flavivirus is West Nile virus (WNV) and said second flavivirus is Japanese Encephalitis virus.

2. A method of inducing an immune response to a pathogenic flavivirus infection in a patient, said method comprising administering to said patient the live-attenuated flavivirus of claim 1.

3. The method of claim 2, wherein said patient does not have, but is at risk of developing, said flavivirus infection.

4. The method of claim 2, wherein said patient has said flavivirus infection.

5. An immunogenic composition comprising the live-attenuated flavivirus of claim 1 and a pharmaceutically acceptable carrier or diluent.

6. A live-attenuated trimeric flavivirus, comprising:
a first flavivirus encoding a membrane precursor gene (prM), envelope gene (E) and a NS1 gene (NS1) from a second flavivirus, wherein (i) said first flavivirus is West Nile virus (WNV), (ii) said second flavivirus is Japanese Encephalitis virus, and (iii) the NS4A protein of the first flavivirus is a mutant NS4A protein having a V29I mutation.

* * * * *